US009913893B2

(12) United States Patent
Berghman et al.

(10) Patent No.: US 9,913,893 B2
(45) Date of Patent: *Mar. 13, 2018

(54) VACCINE VECTORS AND METHODS OF ENHANCING IMMUNE RESPONSES

(71) Applicants: THE BOARD OF TRUSTEES OF THE UNIVERSITY OF ARKANSAS, Little Rock, AR (US); THE TEXAS A&M UNIVERSITY SYSTEM, College Station, TX (US)

(72) Inventors: Luc Berghman, College Station, TX (US); Walter Bottje, Fayetteville, AR (US); Billy Hargis, Fayetteville, AR (US); Sherryll Layton, Rogers, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/623,105

(22) Filed: Feb. 16, 2015

(65) Prior Publication Data

US 2015/0190500 A1 Jul. 9, 2015

Related U.S. Application Data

(63) Continuation of application No. 13/574,504, filed as application No. PCT/US2011/022062 on Jan. 21, 2011, now Pat. No. 8,956,618.

(60) Provisional application No. 61/297,098, filed on Jan. 21, 2010.

(51) Int. Cl.
| | | |
|---|---|---|
| *A61K 39/145* | (2006.01) | |
| *A61K 39/12* | (2006.01) | |
| *C12N 7/00* | (2006.01) | |
| *A61K 48/00* | (2006.01) | |
| *A61K 39/00* | (2006.01) | |

(52) U.S. Cl.
CPC ............ *A61K 39/145* (2013.01); *A61K 39/12* (2013.01); *C12N 7/00* (2013.01); *A61K 48/00* (2013.01); *A61K 2039/522* (2013.01); *A61K 2039/523* (2013.01); *A61K 2039/542* (2013.01); *A61K 2039/543* (2013.01); *A61K 2039/6006* (2013.01); *C12N 2760/16034* (2013.01)

(58) Field of Classification Search
None
See application file for complete search history.

(56) References Cited

U.S. PATENT DOCUMENTS

| | | | |
|---|---|---|---|
| 5,683,700 | A | 11/1997 | Charles et al. |
| 5,747,309 | A | 5/1998 | Allan et al. |
| 5,962,406 | A | 10/1999 | Armitage et al. |
| 5,981,724 | A | 11/1999 | Armitage et al. |
| 6,087,329 | A | 7/2000 | Armitage et al. |
| 6,190,669 | B1 | 2/2001 | Noriega et al. |
| 6,264,951 | B1 | 7/2001 | Armitage et al. |
| 6,306,387 | B1 | 10/2001 | Galan |
| 6,410,711 | B1 | 6/2002 | Armitage et al. |
| 6,479,258 | B1 | 11/2002 | Short |
| 6,713,279 | B1 | 3/2004 | Short |
| 6,902,906 | B1 | 6/2005 | Chatfield |
| 6,923,957 | B2 | 8/2005 | Lowery et al. |
| 6,923,958 | B2 | 8/2005 | Xiang et al. |
| 6,936,425 | B1 | 8/2005 | Hensel et al. |
| 6,969,609 | B1 | 11/2005 | Schlom et al. |
| 7,087,573 | B1 | 8/2006 | Lazarus et al. |
| 7,332,298 | B2 | 2/2008 | Kornbluth |
| 7,371,392 | B2 | 5/2008 | Tripp et al. |
| 7,405,270 | B2 | 7/2008 | Armitage et al. |
| 7,495,090 | B2 | 2/2009 | Prussak et al. |
| 7,842,501 | B2 | 11/2010 | Cai et al. |
| 7,928,213 | B2 | 4/2011 | Prussak et al. |
| 8,604,178 | B2 | 12/2013 | Bottje et al. |
| 8,956,618 | B2 | 2/2015 | Berghman et al. |
| 8,956,849 | B2 | 2/2015 | Bottje et al. |
| 8,961,990 | B2 | 2/2015 | Hargis et al. |
| 2001/0021386 | A1 | 9/2001 | Nuijten et al. |
| 2003/0045492 | A1 | 3/2003 | Tang et al. |
| 2003/0165538 | A1 | 9/2003 | Goldman et al. |
| 2004/0006006 | A9 | 1/2004 | Armitage et al. |

(Continued)

FOREIGN PATENT DOCUMENTS

| | | |
|---|---|---|
| WO | WO 1993/008207 | 4/1993 |
| WO | WO 1995/014487 | 6/1995 |
| WO | WO 1996/026735 | 9/1996 |
| WO | WO 1996/040918 | 12/1996 |
| WO | WO 1999/027948 | 6/1999 |
| WO | WO 1999/032138 | 7/1999 |
| WO | WO 1999/059609 | 11/1999 |
| WO | WO 2000/063395 | 10/2000 |
| WO | WO 2000/063405 | 10/2000 |
| WO | WO 2001/042298 | 6/2001 |

(Continued)

OTHER PUBLICATIONS

GenBank Accession #ACD37491, matrix protein 2, partial [Influenza A virus (A/Brisbane/59/2007(H1N1))], May 2008.*

(Continued)

*Primary Examiner* — Benjamin P Blumel
(74) *Attorney, Agent, or Firm* — Andrus Intellectual Property Law, LLP

(57) ABSTRACT

Provided herein are vaccine vectors including an antigenic polypeptide and an HMGB1 polypeptide present on the surface of the vaccine vector. Compositions comprising the vaccine vectors are also provided and include a pharmaceutically acceptable carrier, suitably a carrier for oral or nasal administration. Also provided are methods of enhancing immune responses, in particular antibody immune response and suitably an IgA response, by administering the vaccine vectors or compositions disclosed herein to a subject.

17 Claims, 9 Drawing Sheets

(56) References Cited

U.S. PATENT DOCUMENTS

| | | |
|---|---|---|
| 2004/0047873 A1 | 3/2004 | Al-Shamkhani et al. |
| 2004/0053841 A1 | 3/2004 | Tracey et al. |
| 2004/0141948 A1 | 7/2004 | O'Keefe |
| 2004/0156851 A1 | 8/2004 | Newman |
| 2004/0203039 A1 | 10/2004 | Hensel et al. |
| 2004/0242481 A1 | 12/2004 | Bianchi et al. |
| 2005/0181994 A1 | 8/2005 | Chamberlain et al. |
| 2005/0226888 A1 | 10/2005 | Deisseroth et al. |
| 2006/0014248 A1 | 1/2006 | Marshall et al. |
| 2006/0078994 A1 | 4/2006 | Healey et al. |
| 2006/0121047 A1 | 6/2006 | Tracey |
| 2006/0233829 A1 | 10/2006 | Curtiss |
| 2006/0286074 A1 | 12/2006 | Tang et al. |
| 2007/0025982 A1 | 2/2007 | Ledbetter et al. |
| 2007/0082400 A1 | 4/2007 | Healey et al. |
| 2007/0128183 A1 | 6/2007 | Meinke et al. |
| 2007/0128223 A1 | 6/2007 | Tang et al. |
| 2007/0237779 A1 | 10/2007 | Ledbetter et al. |
| 2007/0249553 A1 | 10/2007 | Newell et al. |
| 2008/0004207 A1 | 1/2008 | Tsung et al. |
| 2008/0069821 A1 | 3/2008 | Yang et al. |
| 2008/0075728 A1 | 3/2008 | Newman |
| 2008/0124320 A1 | 5/2008 | O'Keefe |
| 2008/0305120 A1 | 12/2008 | Messmer et al. |
| 2009/0004194 A1 | 1/2009 | Kedl |
| 2010/0040608 A1 | 2/2010 | Wahren-Herlenius et al. |
| 2010/0047231 A1 | 2/2010 | Zabaleta Azpiroz et al. |
| 2010/0074915 A1 | 3/2010 | Haynes |
| 2010/0112002 A1 | 5/2010 | Lien et al. |
| 2010/0196419 A1 | 8/2010 | Compans et al. |
| 2010/0233152 A1 | 9/2010 | Bullerdick |
| 2010/0291109 A1 | 11/2010 | Kedl |
| 2010/0292309 A1 | 11/2010 | Vile et al. |
| 2011/0020318 A1 | 1/2011 | Tracey et al. |
| 2011/0159026 A1 | 6/2011 | Bottje et al. |

FOREIGN PATENT DOCUMENTS

| | | |
|---|---|---|
| WO | WO 2001/056602 | 8/2001 |
| WO | WO 2002/036769 | 5/2002 |
| WO | WO 2002/092773 | 11/2002 |
| WO | WO 2003/026691 | 4/2003 |
| WO | WO 2003/099340 | 12/2003 |
| WO | WO 2004/009615 | 1/2004 |
| WO | WO 2005/025604 | 3/2004 |
| WO | WO 2004/046338 | 6/2004 |
| WO | WO 2004/046345 | 6/2004 |
| WO | WO 2005/035570 | 4/2005 |
| WO | WO 2005/058950 | 6/2005 |
| WO | WO 2005/113598 | 12/2005 |
| WO | WO 2006/012373 | 2/2006 |
| WO | WO 2006/042177 | 4/2006 |
| WO | WO 2007/011606 | 4/2006 |
| WO | WO 2006/069262 | 6/2006 |
| WO | WO 2006/105972 | 10/2006 |
| WO | WO 2007/042583 | 4/2007 |
| WO | WO 2007/054658 | 5/2007 |
| WO | WO 2007/056266 | 5/2007 |
| WO | WO 2007/103048 | 9/2007 |
| WO | WO 2007/117682 | 10/2007 |
| WO | WO 2008/036675 | 3/2008 |
| WO | WO 2008/109825 | 9/2008 |
| WO | WO 2009/059018 | 5/2009 |
| WO | WO 2009/059298 | 5/2009 |
| WO | WO 2011/156619 | 12/2011 |
| WO | 2013/071298 | 5/2013 |

OTHER PUBLICATIONS

GenBank Accession # AAD52670, high mobility group protein HMG1 [Gallus gallus], Sep. 2000.*

Duc, L.H. et al., "'Bacterial Spores as Vaccine Vehicles," Infection and Immunity (2003) 71(5): 2810-2818.

Faham, A. et al., "Liposomal Ag engrafted with peptides of sequence derived front HMGB1 induce potent Ag-specific and anti-tumour immunity" (2009) 2(42):5846-5854.

Hoang, T.H. et al., "'Recombinant Bacillus subtilis Expressing the Clostridium perfringens Alpha Toxoid is a Candidate Orally Delivered Vaccine against Necrotic Enteritis," Infection and immunity (2008) 76(11): 5257-5265.

Muthumani, G. et al., "Co-immunization with an optimized plasmid-encoded immune stimulatory interleukin, high-mobility group box 1 protein, results in enhanced interferon-y secretion by antigen-specific CD8 T cells," Immunology (2009) 128: e612-e620.

Uyen, N.Q. et al., "Enhanced immunization and expression strategies using bacterial spores as heat-stable vaccine delivery vehicles," vaccine (2007) 25 356-365.

Agterberg, M. et al., "Outer membrane protein PhoE as a carrier for the exposure of foreign antigenic determinants at the bacterial cell surface," Antonie Van Leeuwenhoek (1991). 59(4):249-262.

Al-Ramadi, B. K. et al., "Induction of innate immunity by IL-2 expressing *Salmonella* confers protection against letal challenge," Mol. Immunol. (2003) 39:763-770.

Al-Ramadi, B. K. et al., "Influence of vector-encoded cytokines on anti-*Salmonella* immunity: divergent effects of interleukin-2 and tumor necrosis factor alpha," Infect. Immun. (2001) 69:3960-3988.

Andeersson, U. et al., "HMGB1 is a therapeutic target for sterile inflammation and infection," Annu. Rev. Immunol. (2011) 29:139-162.

Babu, U., et al., "*Salmonella enteritidis* clearance and immune responses in chickens following *Salmonella* vaccination and challenge." Vet. Immunol. Immunopathol, (2004)101:251-257.

Barr, T.A. et al., "A potent adjuvant effect of CD40 antibody attached to antigen," Immunology (2003) 109:87-92.

Barrow, P. A., et al., "Reduction in faecal excretion of *Salmonella typhimurium* strain F98 in chickens vaccinated with live and killed *S. typhimurium*organisms," Epidemiol, Infect. (1990) 104:413-426.

Black, R.A. et al., "Antibody response to the M2 protein of influenza A virus expressed in insect cells," J. Gen, Virol. (1993) 74(Pt.1):143-146.

Blomfield, I.C. et al., "Allelic exchange in *Escherichia coli* using the Bacillus subtilis sacB gene and a temperature-sensitive pSC101 replicon," Mol Microbiol (1991) 5(6):1447-1457.

Buckley, A.M. et al., "Evaluation of live-attenuated *Salmonella* vaccines expressing Campylobacter antigens for control of C. jejuni in poultry," (2010) Vaccine 28(4):1094-1105.

Capua, I. et al., "The challenge of avian influenza to the veterinary community," Avian Pathol. (2006) 35:189-205.

Capua, I. et al., "Vaccination for avian influenza in Asia," Vaccine (2004) 22:4137-4138.

Capua, I. et al, "Control of avian influenza in poultry," Emerg. Infect. Dis. (2006) 12:1319-1324.

Charbit, A. et al., "Probing the topology of a bacterial membrane protein by genetic insertion of a foreign epitope; expression at the cell surface," EMBO J (1986) 5(11):3029-3037.

Charbit, A. et al., "Versatility of a vector for expressing foreign polypeptides at the surface of gram-negative bacteria," Gene (1988) 70(1):181-189.

Chatfield et al., "The development of oral vaccines based on live attenuated *Salmonella* strains." FEMS Immunol. Med. Microbiol. (1993) 7:1-7.

Cole, K. et al., "Evaluation of a novel recombinant *Salmonella* vaccine vector for avian influenza," Poultry Science (2007) 86(Supp.1):585-586.

Cox, M.M. et al., "Scarless and site-directed mutagenesis in *Salmonella enteritidis* chromosome," BMC Biotech. (2007) 7(59):10 pages.

Crawford, J., et al., "Baculovirus-derived hemaggllinin vaccines protect against lethal influenza infections by avian H5 and H7 subtypes," Vaccine (1999) 17:2265-2274.

De Filette, M. et al, "The universal influenza vaccine M2e-HBc administered intrallasally in combination with the adjuvant CTA1-DD provides complete protection," Vaccine (2006) 24:544-551.

De Filette, M. et al., "Universal influenza A vaccine: Optimization of M2-based constructs," Virology (2005) 337:149-161.

(56) References Cited

OTHER PUBLICATIONS

De Filette M. et al., "Improved design and intranasal delivery of an M2e-base: human influenza A vaccine," Vaccine (2006) 24:6597-6601.
Dumitriu, I.E. et al., "HMGB1: guiding immunity from within," Trends Immunol. (2005) 26(7):381-387.
Ellis, R.W., "New technologies for making vaccines," (1988) Vaccines, Chapter 29:568-574.
Ernst, W.A. et al., "Protection against H1, H5, H6 and H9 influenza A infection with liposomal matrix 2 epitope vaccines," Vaccine (2006) 24:5158-5168.
Faham, A. et al., "Liposomal Ag engrafied with peptides of sequence derived froml HMGB1 induce potent Ag-specific and anti-tumor immunity," (2009) 27(42):5846-5854.
Fan, J. et al., "Preclinical study of influenza virus A M2 peptide conjugate vaccines in mice, ferrets and rhesus monkeys," Vaccine (2004) 22:293-3003.
Farnell, M.B. et al., "Upregulation of oxidative burst and degranulation in chicken heterophils stimulated with probiotic bacteria," Poult. Sci. (2006) 85:1900-1906.
Fecteau, J.F. et al., "CD40 Stimulation of Human Peripheral B Lymphocytes; Distinct Response from Naïve and Memory Cells," J Immunol (2003) 171:4621-4629.
Fernandez-Cabezudo et al., "Evidence for the requirement for CD40-CD154 interactions in resistance to infections with attenuated *Salmonella*" J. Endotoxin Res. (2005) 11:395-399.
Fiers, W. et al., "A universal human influenza A vaccine," Virus Research (2004) 103:173-176.
Frace, A.M. et al., "Modified M2 proteins produce heterotypic immunity against influenza A virus," Vaccine (1999) 17:2237-2244.
Gao, W. et al., "Protection of mice and poultry from lethal H5N1 avian influenza virus through adenovirus-base immunization," J. Virol. (2006) 80:1959-1964.
Gares, S.L. et al., "Immunotargeting with CD154 (CD40 ligand) enhances DNA vaccine reponses in ducks," Clin. Vaccine Immun. (2006) 13:958-965.
Gast, R.K. et al., "The relationship between the magnitude of the specific antibody response to experimental *Salmonella enteritidis* enteritidis infection in laying hens and their production of contaminated eggs," Avian Diseases (2001) 45:425-431.
GenBank AAQ77437, "matrix protein 2, partial [Influenza A virus (A/chicken/Chile/4957/02(H7N3))]," Mar. 3, 2004.
GenBank AFI 78849, "High mobility group protein HMG1 [Gallus gallus]," Sep. 27, 2000.
GenBank ABW06338, "Matrix protein 2, partial [Influenza A virus (A/Indonesia/195H/2005(H5N1))]," May 1, 2008.
Grangette, C. et al., Protection against tetanus toxin after intragastric adminstration of two recombinant lactic acid bacteria: Impact and strain viability and in vivo persistence, Vaccine (2002) 20:3304-3309.
Greenspan, N.S. et al., "Defining epitopes: It's not as easy as it seems," Nature Biotechnol. (1999) 17:936-937.
Grewal, I.S. et al., CD40 and CD154 in cell-mediated immunity Annu. Rev. Immunology. (1998)16:111-35.
Harcourt, J.L. et al., "CD40 ligand (CD154) improves the durability of respiratory syncytial virus DNA vaccination in BALB/c mice," Vaccine (2003) 21(21-22):2964-2979.
Hargis, B, "Live Recombinant *Salmonella* Vaccination with Novel Universal Antigen Presentation and Immune Protection," USDA Grant Project Status, Jan. 14, 2012.
Harris, H.E., et al., "Mini-review: The nuclear protein HMGBI as a proinflammatory mediator," (2004) European J. of Immunology 34:1503-1512.
Hayes, L.J. et al., "Chiamydia trachomatis major outer membrane protein epitopes expressed as fusions with LamB in an attenuated aro A strain of *Salmonella typhimurium*; their application as potential immunogens," Journal of General Microbiology (1991) 137:1557-1564.

Heinen, P.P. et al., "Vaccination of pigs with a DNA construct expressing an influenza virus M2-nucleoprotein fusion protein exacerbates disease after challenge with influenza A virus" Journal of General Virology (2002) 83(8):1851-1859.
Holmgren, J. et al., "Mucosal immunity: implications for vaccine development," Immunobiol. (1992) 184:157-179.
Husseiny, M.L. et al., "Rapid method for the construction of *Salmonella enterica*serovar typhimurium vaccine carrier strains," Infec. Immun. (2005) 73(3):1598-1605.
Kaiser. J., "A one-size-fits-all flu vaccine?, " Science (2006) 312:380-382.
Katz, J.M. et al., "Adjuvant activity of the heat-labile enterotoxin front enterotoxigenic *Escherichia coli* for oral administration of inactivated influenza virus vaccine," J. Infect. Dis. (1997) 175:352-363.
Kim, E.-H. et al., "Prokaryote-expressed M2e protein improves H9N2 influenza vaccine efficacy and protection against lethal influenza in virus in mice," Virol, J., (2013) 10(104):1-11.
Kimura, R. et al., "Enhancement of antibody response by high mobility group box protein-1-based DNA immunization" J. of Immunol. Methods (2010) 361:21-30.
Koch, F. et al., "High level IL-12 production by murine dendritic cells: upregutation via MHC class II and CD40 molecules and downregulation by IL-4 and IL-10," J. Exp. Med. (1996) 184:741-746.
Kodihalli, S. et al., "Cross-protection among lethal H5N2 influenza viruses induced by DNA vaccine to the hemagglutinin," J. Virol. (1997) 71:3391-3396.
Kotton, C.N. et al., "Enteric pathogens as vaccine vectors for foreign antigen delivery," Infect. Immun.(2004) 77:5535-5547.
Kwon, Y.M. et al., "*Salmonella*-based vaccines for infectious diseases," Expert Review of Vaccines (2007) 6(2):147-152.
Lavelle, E.C. et al., "Delivery systems and adjuvants for oral vaccines," Expert Opin, Drug Deliv. (2006) 3(6):747-762.
Layton, S.L., et al., "Vaccination of chickens with recombinant *Salmonella* expressing M2e and CD154 epitopes increases protection and decreases viral shedding after low pathogenic avian influenza challenge," Poultry Science (2009) 88(11):2244-2252.
Layton et al., Evaluation of *Salmonella* vectored Campylobacter peptide epitopes for reduction of Campylobacter jejuni in broiler chickens, Clin. Vaccine Immnunol. (2011) 18(3):449-454.
Lee, J. et al., "Mucosal immunization with surface-displayed severe acute respiratory syndrome coronavirus spike protein on Lactobacillus casei induces neutralizing antibodies in mice," J. Virol. (2006) 80:4079-4087.
Lee, J.S. et al., "Surface-displayed viral antigens on *Salmonella* carrier vaccine," Nat. Biotechnol. (2000) 18:645-648.
Li, W., "Synergistic antibody induction by antigen-CD40 ligand fusion protein as improved immunogen," Immunology (2005) 115(2):215-222.
Liu, W. et al., "Monoclonal antibodies recognizing EVETPIRN epitope of influenza A virus M2 protein could protect mice from lethal influenza A virus challenge," Immunol. Lett. (2004) 93:131-136.
Liu, W. et al., "Sequence comparison between the extracellular domain of M2 protein human and avian influenza A virus provides new information for bivalent influenza vaccine design," Microbes and Infection (2005) 7:171-177.
Liu, M. et al., "Display of avian influenza virus nucleoprotein on *Bacillus thuringiensis* cell surface using CTC as a fusion partner," Applied Genetics and Molecular Biotechnology (2008) 78:669-676.
Lowe, D.C. et al., "Characterization of candidate live oral *Salmonella typhi* vaccine strains harboring defined mutations in aroA, aroC, and htrA," Infection and Immunity (1999) Feb.:700-707.
Mann, J.F. et al., "Delivery systems: a vaccine strategy for overcoming, mucosal tolerance?" Expert Rev. Vaccines (2009) 8(1):103-112.
Manoj, S. et al., "Targeting with Bovine CD154 enhances Immoral immune responses induced by a DNA vaccine in sheep," (2003) Journal of Immunology 170:989-996.
Mauriello, E.M.F. et al., "Display of heterologous antigens on the Bacillus subtilis spore coat using CotC as a fusion partner," (2004) Vaccine 22(9-10):1177-1187.

(56) References Cited

OTHER PUBLICATIONS

Mendoza, R.B. et al., "Cutting edge: Immunostimulatory effects of a plasmid expressing CD40 ligand (CD154) on gene immunization," Journal of Immunology (1997) 159(12):5777-5781.

Miga, A. et al., "The role of CD40-CD154 interactions in the regulation of cell mediated immunity," Immunol. Invest. (2000) 29:111-114.

Mogensen, T.H., "Pathogen recognition and infirtmmatory signaling in innate immune defenses," Clin. Microbiol. Rev. (2009) 22(2):240-273.

Mohamadzadeh M. et al., "Targeting mucosal dendritic cells with microbial antigens from probiotic lactic acid bacteria," Expert Rev. Vaccines (2008) 7(2):163-174.

Moyle, P.M. et al., "Mucosal immunisation: adjuvants and delivery systems," Curr. Drug Deliv. (2004) 1(4):385-396.

Mozdzanowska, K. et al., "Induction of influenza type A virus-specific resistance by immunization of mice with a synthetic multiple antigenic peptide vaccine that contains ectodomains of matrix protein 2," Vaccine (2003) 21:2616-2626.

Nakajima, A. et al., "Antitumor effect of CD40 ligand: Elicitation of local and systemic antitumor responses by IL-12 and B7," (1998) Journal of Immunology 161:1901-1907.

Neirynck, S. et al., "A universal influenza A vaccine based on the extracellular domain of the M2 protein," Nat. Med., (1999) 5:1157-1163.

Ninomiya, A. et al., "Intranasal administration of a synthetic peptide vaccine encapsulated in liposome together with an anti-CD40 antibody induces protective immunity against influenza A virus in mice," Vaccine (2002) 20:3123-3129.

O'Callaghan, D. et al., "Immunogenicity of foreign peptide epitopes expressed in bacterial envelope proteins," Research in Microbiology (1990) 141:963-969.

Ochoa-Reparaz J. et al., "Humoral immune reponse in hens naturally infected with *Salmonella enteritidis* against outer membrane proteins and other surface structural antigens," (2004) Vet. Res. 35:291-298.

Palese, P. et al., "Influenza vaccines: present and future," J. Clin. Invest. (2002) 110:9-13.

Pasetti. M. et al., "Animal models paving the way for clinical trials of attenuated *Salmonella enterica* servoar Typhi live oral vaccines and live vectors," Vaccine (2013) 21:401-418.

Pisetsky, D.S. et al., "High-mobility group box protein 1 (HMGB1): an alarmin mediating the pathogenesis of rheumatic disease." Arthritis Res. Ther. (2008) 10(3):209.

Rabsch, W. et al., "Competitive exclusion of *Salmonella enteritidis* by *Salmonella gallinarum* in poultry," Emerging Inf. Diseases (2000) 6(5):443-448.

Rovere-Quereni, P. et al., "HMGB1 is an endogenous immune adjuvant released by necrotic cells," EMBO Rep. (2004) 5(8):825-830.

Russmann, H. et al., "Delivery of epitopes by the *Salmonella* type III secretion system for vaccine development," Science (1998) 281(5376):565-568.

Saenz, R. et al., "HMGB1-derived peptide acts as adjuvant inducing immune responses to peptide and protein antigen," (2010) Vaccine 28(47):7556-7562.

Slepuseiken, V.A. et al., "Protection of mice against influenza A virus challenge by vaccination with baculovirus-expressed M2 protein" Vaccine (1995) 13:1399-1402.

Su, G.F. et al., "Construction of stable LamB-Shiga toxin B subunit hybrids: analysis of expression in *Salmonella typhinntrium* aroA strains and stimulation of B subunit-specific mucosal and serum antibody responses," Infect Immun (1992) 60(8):3345-3359.

Swayne. D.E. et al., "Protection against diverse highly pathogenic H5 avian influenza viruses in chickens immunized with a recombinant fowlpox vaccine containing an H5 avian influenza hemagglutinin gene insert," Vaccine (2000) 18:1088-1095.

Swayne, D.E., "Vaccines for List A poultry diseases: emphasis on avian influenza," Dev. Biol. (2003) 114:201-212.

Tang, M. et al., "Recombinant adenovirus encoding the HA gene from swine H3N2 influenza virus partially protects mice from challenge with heterologons virus: A/HK/1/68 (H3N2)," Arch. Virol. (2002) 147:2125-2141.

Tompkins, S.M. et al., "Matrix protein 2 vaccination and protection against influenza viruses, including subtype H5N1," Emerging Infectious Diseases (2007) 13(3):426-435.

Tregaskes, C.A. et al., "Conservation of biological properties of the CD40 ligand, CD154 in a non-mammalian vertebrate," Dev. Comp. Immunol. (2005) 29:361-374.

Tumpey, T.M. et al., "Comparative susceptibility of chickens and turkeys to avian influenza A H7N2 virus infection and protective efficacy of a commerical avian influenza H7N2 virus vaccine," Avian Dis. (2004) 48(1):167-176.

Ulloa, L. et al., "High-mobility group box 1 (HMGB1) protein: friend and foe," Cytokine Growth Factor Rev. (2006) 17(3):189-201.

Vega, M.L. et al., "A *Salmonella typhi*OmpC fusion protein expressing the CD154 Trp140-Ser149 amino acid strand binds CD40 and activates a lymphoma B-cell line," Immunol. (2003) 110:206-216.

Verjans, G.M. et al., "Intracellular processing and presentation of T cell epitopes, expressed by recombinant *Escherichia coil* and *Salmonella typhimurium*, to human T cells," Eur J Immunol (1995) 25(2):405-410.

Vierira-Pinto, M. et al., "Occurrence of *Salmonella* in the ileum, ileocolic lymph nodes, tonsils, mandibular lymph nodes and carcasses of pigs slaughtered for consumption," J Vet Med B Infection Dis Vet Public Health (2005) 52(10):476-81.

Wang, J. et al., "Immunogenicity of viral B-cell epitopes inserted into two surface loops of the *Escherichia coli* K12 LamB protein and expressed in an attenuated aroA strain of *Salmonella typhimariurn*" Vaccine (1999) 17(1):1-12.

Xu, Y. et al., "The role of CD40-CD154 interaction in cell inununoregulation," J. Biomed. Sci. (2004) 11:426-438.

Zebedee, S.L. et al., "Influenza A virus M2 protein: monoclonal antibody restriction of virus growth and detection of M2 in virions," J. Virol. (1988) 62:2762-2772.

Zharikova, D. et al., "Influenza type A virus escape mutants emerge in vivo in the presence of antibodies to the ectodomain of matrix protein 2," (2005) 79:6644-6654.

Zou, P. et al., "The epitope recognized by a monoclonal antibody in influenza A virus M2 protein is immunogenic and confers immune protection," Int. Immunopharmacol. (2005) 5:631-635.

International Search Report and Written Opinion of the International Searching Authority for Application No. PCT/US07/78785 dated Sep. 29, 2008 (11 pages).

International Search Report and Written Opinion for Application No. PCT/US08/81813 dated May 12, 2009 (13 pages).

International Search Report and Written Opinion of the International Searching Authority for Application No. PCT/US11/22062 dated Mar. 29, 2011 (11 pages).

International Search Report and Written Opinion of the International Searching Authority for Application No. PCT/US11/39832 dated Nov. 23, 2011 (15 pages).

Extended European Search Report for European Patent Application No. 11735230.2 dated Sep. 24, 2013 (8 pages).

Office Action for U.S. Appl. No. 13/574,504 dated Dec. 12, 2013 (14 pages).

Office Action for U.S. Appl. No. 13/574,504 dated Jun. 18, 2014 (12 pages).

Gast, .K., et al., Deposition of Phage Type 4 and 13a *Salmonella enteritidis* strains in the Yolk and Albumen of eggs laid by experimentally infected hens, Avian Diseases, 2000, pp. 706-710, vol. 44:3.

Sinha, K., et al., *Salmonella typhimurium* aroA, htrA, and aroD htrA mutants cause progressive infections in athymic (nu/nu) BALB/c mice, Infection and Immunity, 1997, pp. 1566-69, vol. 65:4.

* cited by examiner

SEQUENCE LISTING

<160> NUMBER OF SEQ ID NOS: 40

<210> SEQ ID NO 1
<211> LENGTH: 24
<212> TYPE: PRT
<213> ORGANISM: Avian influenza virus

```
<220> FEATURE:
<221> NAME/KEY: misc_feature
<223> OTHER INFORMATION: M2e

<400> SEQUENCE: 1

Met Ser Leu Leu Thr Glu Val Glu Thr Pro Thr Arg Asn Gly Trp Glu
1               5                   10                  15

Cys Lys Cys Ser Asp Ser Ser Asp
            20

<210> SEQ ID NO 2
<211> LENGTH: 24
<212> TYPE: PRT
<213> ORGANISM: Avian Influenza virus
<220> FEATURE:
<221> NAME/KEY: misc_feature
<223> OTHER INFORMATION: M2e

<400> SEQUENCE: 2

Met Ser Leu Leu Thr Glu Val Glu Thr Pro Thr Arg Asn Glu Trp Gly
1               5                   10                  15

Cys Arg Cys Asn Asp Ser Ser Asp
            20

<210> SEQ ID NO 3
<211> LENGTH: 24
<212> TYPE: PRT
<213> ORGANISM: Avian Influenza virus
<220> FEATURE:
<221> NAME/KEY: misc_feature
<223> OTHER INFORMATION: M2e

<400> SEQUENCE: 3

Met Ser Leu Leu Thr Glu Val Glu Thr Pro Ile Arg Asn Glu Trp Gly
1               5                   10                  15

Cys Arg Cys Asn Asp Ser Ser Asp
            20

<210> SEQ ID NO 4
<211> LENGTH: 24
<212> TYPE: PRT
<213> ORGANISM: Avian Influenza virus
<220> FEATURE:
<221> NAME/KEY: misc_feature
<223> OTHER INFORMATION: M2e

<400> SEQUENCE: 4

Met Ser Leu Leu Thr Glu Val Glu Thr Pro Thr Arg Asn Gly Trp Glu
1               5                   10                  15

Cys Arg Cys Asn Asp Ser Ser Asp
            20

<210> SEQ ID NO 5
<211> LENGTH: 8
<212> TYPE: PRT
<213> ORGANISM: Avian Influenza virus
<220> FEATURE:
<221> NAME/KEY: misc_feature
<223> OTHER INFORMATION: M2e

<400> SEQUENCE: 5

Glu Val Glu Thr Pro Ile Arg Asn
1               5
```

<210> SEQ ID NO 6
<211> LENGTH: 8
<212> TYPE: PRT
<213> ORGANISM: Avian Influenza virus
<220> FEATURE:
<221> NAME/KEY: misc_feature
<223> OTHER INFORMATION: M2e

<400> SEQUENCE: 6

Glu Val Glu Thr Pro Thr Arg Asn
1               5

<210> SEQ ID NO 7
<211> LENGTH: 12
<212> TYPE: PRT
<213> ORGANISM: Avian Influenza virus
<220> FEATURE:
<221> NAME/KEY: misc_feature
<223> OTHER INFORMATION: HA5 UA

<400> SEQUENCE: 7

Leu Leu Ser Arg Ile Asn His Phe Glu Lys Ile Gln
1               5                   10

<210> SEQ ID NO 8
<211> LENGTH: 19
<212> TYPE: PRT
<213> ORGANISM: Avian Influenza virus
<220> FEATURE:
<221> NAME/KEY: misc_feature
<223> OTHER INFORMATION: HA5 LB

<400> SEQUENCE: 8

Ala Asn Pro Ala Asn Asp Leu Cys Tyr Pro Gly Asp Phe Asn Asp Tyr
1               5                   10                  15

Glu Glu Leu

<210> SEQ ID NO 9
<211> LENGTH: 16
<212> TYPE: PRT
<213> ORGANISM: Avian Influenza virus
<220> FEATURE:
<221> NAME/KEY: misc_feature
<223> OTHER INFORMATION: NP 54-69

<400> SEQUENCE: 9

Gly Arg Leu Ile Gln Asn Ser Ile Thr Ile Glu Arg Met Val Leu Ser
1               5                   10                  15

<210> SEQ ID NO 10
<211> LENGTH: 14
<212> TYPE: PRT
<213> ORGANISM: Avian Influenza virus
<220> FEATURE:
<221> NAME/KEY: misc_feature
<223> OTHER INFORMATION: NP 147-160

<400> SEQUENCE: 10

Thr Tyr Gln Arg Thr Arg Ala Leu Val Arg Thr Gly Met Asp
1               5                   10

<210> SEQ ID NO 11
<211> LENGTH: 272
<212> TYPE: PRT
<213> ORGANISM: Gallus gallus
<220> FEATURE:
<221> NAME/KEY: misc_feature
<223> OTHER INFORMATION: CD154 chicken

<400> SEQUENCE: 11

Met Asn Glu Ala Tyr Ser Pro Ala Ala Pro Arg Pro Met Gly Ser Thr
1               5                   10                  15

Ser Pro Ser Thr Met Lys Met Phe Met Cys Phe Leu Ser Val Phe Met
            20                  25                  30

Val Val Gln Thr Ile Gly Thr Val Leu Phe Cys Leu Tyr Leu His Met
        35                  40                  45

Lys Met Asp Lys Met Glu Glu Val Leu Ser Leu Asn Glu Asp Tyr Ile
    50                  55                  60

Phe Leu Arg Lys Val Gln Lys Cys Gln Thr Gly Glu Asp Gln Lys Ser
65                  70                  75                  80

Thr Leu Leu Asp Cys Glu Lys Val Leu Lys Gly Phe Gln Asp Leu Gln
                85                  90                  95

Cys Lys Asp Arg Thr Ala Ser Glu Glu Leu Pro Lys Phe Glu Met His
            100                 105                 110

Arg Gly His Glu His Pro His Leu Lys Ser Arg Asn Glu Thr Ser Val
        115                 120                 125

Ala Glu Glu Lys Arg Gln Pro Ile Ala Thr His Leu Ala Gly Val Lys
    130                 135                 140

Ser Asn Thr Thr Val Arg Val Leu Lys Trp Met Thr Thr Ser Tyr Ala
145                 150                 155                 160

Pro Thr Ser Ser Leu Ile Ser Tyr His Glu Gly Lys Leu Lys Val Glu
                165                 170                 175

Lys Ala Gly Leu Tyr Tyr Ile Tyr Ser Gln Val Ser Phe Cys Thr Lys
            180                 185                 190

Ala Ala Ala Ser Ala Pro Phe Thr Leu Tyr Ile Tyr Leu Tyr Leu Pro
        195                 200                 205

Met Glu Glu Asp Arg Leu Leu Met Lys Gly Leu Asp Thr His Ser Thr
    210                 215                 220

Ser Thr Ala Leu Cys Glu Leu Gln Ser Ile Arg Glu Gly Gly Val Phe
225                 230                 235                 240

Glu Leu Arg Gln Gly Asp Met Val Phe Val Asn Val Thr Asp Ser Thr
                245                 250                 255

Ala Val Asn Val Asn Pro Gly Asn Thr Tyr Phe Gly Met Phe Lys Leu
            260                 265                 270

<210> SEQ ID NO 12
<211> LENGTH: 261
<212> TYPE: PRT
<213> ORGANISM: Homo sapiens
<220> FEATURE:
<221> NAME/KEY: misc_feature
<223> OTHER INFORMATION: Human CD154

<400> SEQUENCE: 12

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

```
Leu Leu Asn Cys Glu Glu Ile Lys Ser Gln Phe Glu Gly Phe Val Lys
             85                  90                  95
Asp Ile Met Leu Asn Lys Glu Glu Thr Lys Lys Glu Asn Ser Phe Glu
            100                 105                 110
Met Gln Lys Gly Asp Gln Asn Pro Gln Ile Ala Ala His Val Ile Ser
        115                 120                 125
Glu Ala Ser Ser Lys Thr Thr Ser Val Leu Gln Trp Ala Glu Lys Gly
    130                 135                 140
Tyr Tyr Thr Met Ser Asn Asn Leu Val Thr Leu Glu Asn Gly Lys Gln
145                 150                 155                 160
Leu Thr Val Lys Arg Gln Gly Leu Tyr Tyr Ile Tyr Ala Gln Val Thr
                165                 170                 175
Phe Cys Ser Asn Arg Glu Ala Ser Ser Gln Ala Pro Phe Ile Ala Ser
            180                 185                 190
Leu Cys Leu Lys Ser Pro Gly Arg Phe Glu Arg Ile Leu Leu Arg Ala
        195                 200                 205
Ala Asn Thr His Ser Ser Ala Lys Pro Cys Gly Gln Gln Ser Ile His
    210                 215                 220
Leu Gly Gly Val Phe Glu Leu Gln Pro Gly Ala Ser Val Phe Val Asn
225                 230                 235                 240
Val Thr Asp Pro Ser Gln Val Ser His Gly Thr Gly Phe Thr Ser Phe
                245                 250                 255
Gly Leu Leu Lys Leu
            260

<210> SEQ ID NO 13
<211> LENGTH: 11
<212> TYPE: PRT
<213> ORGANISM: Homo sapiens
<220> FEATURE:
<221> NAME/KEY: misc_feature
<223> OTHER INFORMATION: Human CD154 peptide

<400> SEQUENCE: 13

Trp Ala Glu Lys Gly Tyr Tyr Thr Met Ser Cys
1               5                   10

<210> SEQ ID NO 14
<211> LENGTH: 11
<212> TYPE: PRT
<213> ORGANISM: Gallus gallus
<220> FEATURE:
<221> NAME/KEY: misc_feature
<223> OTHER INFORMATION: Chicken CD154 peptide

<400> SEQUENCE: 14

Trp Met Thr Thr Ser Tyr Ala Pro Thr Ser Ser
1               5                   10

<210> SEQ ID NO 15
<211> LENGTH: 10
<212> TYPE: PRT
<213> ORGANISM: Anas sp.
<220> FEATURE:
<221> NAME/KEY: misc_feature
<223> OTHER INFORMATION: Duck CD154 peptide

<400> SEQUENCE: 15

Trp Asn Lys Thr Ser Tyr Ala Pro Met Asn
1               5                   10
```

```
<210> SEQ ID NO 16
<211> LENGTH: 10
<212> TYPE: PRT
<213> ORGANISM: Mus sp.
<220> FEATURE:
<221> NAME/KEY: misc_feature
<223> OTHER INFORMATION: Mouse CD154 peptide

<400> SEQUENCE: 16

Trp Ala Lys Lys Gly Tyr Tyr Thr Met Lys
 1               5                  10

<210> SEQ ID NO 17
<211> LENGTH: 10
<212> TYPE: PRT
<213> ORGANISM: Bos taurus
<220> FEATURE:
<221> NAME/KEY: misc_feature
<223> OTHER INFORMATION: Cow CD154 peptide

<400> SEQUENCE: 17

Trp Ala Pro Lys Gly Tyr Tyr Thr Leu Ser
 1               5                  10

<210> SEQ ID NO 18
<211> LENGTH: 190
<212> TYPE: PRT
<213> ORGANISM: Gallus gallus
<220> FEATURE:
<221> NAME/KEY: misc_feature
<223> OTHER INFORMATION: Chicken HMGB1 amino acid

<400> SEQUENCE: 18

Met Gly Lys Gly Asp Pro Lys Lys Pro Arg Gly Lys Met Ser Ser Tyr
 1               5                  10                  15

Ala Phe Phe Val Gln Thr Cys Arg Glu Glu His Lys Lys Lys His Pro
             20                  25                  30

Asp Ala Ser Val Asn Phe Ser Glu Phe Ser Lys Cys Ser Glu Arg
         35                  40                  45

Trp Lys Thr Met Ser Ser Lys Glu Lys Gly Lys Phe Glu Asp Met Ala
     50                  55                  60

Lys Ala Asp Lys Leu Arg Tyr Glu Lys Glu Met Lys Asn Tyr Val Pro
 65                  70                  75                  80

Pro Lys Gly Glu Thr Lys Lys Lys Phe Lys Asp Pro Asn Ala Pro Lys
                 85                  90                  95

Arg Pro Pro Ser Ala Phe Phe Leu Phe Cys Ser Glu Phe Arg Pro Lys
             100                 105                 110

Ile Lys Gly Glu His Pro Gly Leu Ser Ile Gly Asp Val Ala Lys Lys
         115                 120                 125

Leu Gly Glu Met Trp Asn Asn Thr Ala Ala Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Val Asp Ala Gly Lys Lys Val Val Ala
                165                 170                 175

Lys Ala Glu Lys Ser Lys Lys Lys Glu Glu Glu Glu Asp
            180                 185                 190

<210> SEQ ID NO 19
<211> LENGTH: 111
<212> TYPE: PRT
<213> ORGANISM: Artificial sequence
```

<220> FEATURE:
<223> OTHER INFORMATION: Synthetic peptide: BS/AI/CD154 =
      HA/NP/M2e/cCD154: SSS serine spacer

<400> SEQUENCE: 19

Ser Ser Ser Thr Tyr Gln Arg Thr Arg Ala Leu Val Arg Thr Gly Met
1 5 10 15

Asp Ser Ser Ser Ala Asn Pro Ala Asn Asp Leu Cys Tyr Pro Gly Asp
20 25 30

Phe Asn Asp Tyr Glu Glu Leu Ser Ser Ser Gly Arg Leu Ile Gln Asn
35 40 45

Ser Ile Thr Ile Glu Arg Met Val Leu Ser Ser Ser Ser Leu Leu Ser
50 55 60

Arg Ile Asn His Phe Glu Lys Ile Gln Ser Ser Ser Glu Val Glu Thr
65 70 75 80

Pro Ile Arg Asn Ser Ser Ser Glu Val Glu Thr Pro Thr Arg Asn Ser
85 90 95

Ser Ser Trp Met Thr Thr Ser Tyr Ala Pro Thr Ser Ser Ser Ser
100 105 110

<210> SEQ ID NO 20
<211> LENGTH: 302
<212> TYPE: PRT
<213> ORGANISM: Artificial sequence
<220> FEATURE:
<223> OTHER INFORMATION: Synthetic peptide: BS/AI/HMGB1 = HA/NP/M2e/HMGB1

<400> SEQUENCE: 20

Ser Ser Ser Thr Tyr Gln Arg Thr Arg Ala Leu Val Arg Thr Gly Met
1 5 10 15

Asp Ser Ser Ser Ala Asn Pro Ala Asn Asp Leu Cys Tyr Pro Gly Asp
20 25 30

Phe Asn Asp Tyr Glu Glu Leu Ser Ser Ser Gly Arg Leu Ile Gln Asn
35 40 45

Ser Ile Thr Ile Glu Arg Met Val Leu Ser Ser Ser Ser Leu Leu Ser
50 55 60

Arg Ile Asn His Phe Glu Lys Ile Gln Ser Ser Ser Glu Val Glu Thr
65 70 75 80

Pro Ile Arg Asn Ser Ser Ser Glu Val Glu Thr Pro Thr Arg Asn Ser
85 90 95

Ser Ser Trp Met Thr Thr Ser Tyr Ala Pro Thr Ser Ser Ser Ser Ser
100 105 110

Met Gly Lys Gly Asp Pro Lys Lys Pro Arg Gly Lys Met Ser Ser Tyr
115 120 125

Ala Phe Phe Val Gln Thr Cys Arg Glu Glu His Lys Lys Lys His Pro
130 135 140

Asp Ala Ser Val Asn Phe Ser Glu Phe Ser Lys Lys Cys Ser Glu Arg
145 150 155 160

Trp Lys Thr Met Ser Ser Lys Glu Lys Gly Lys Phe Glu Asp Met Ala
165 170 175

Lys Ala Asp Lys Leu Arg Tyr Glu Lys Glu Met Lys Asn Tyr Val Pro
180 185 190

Pro Lys Gly Glu Thr Lys Lys Lys Phe Lys Asp Pro Asn Ala Pro Lys
195 200 205

Arg Pro Pro Ser Ala Phe Phe Leu Phe Cys Ser Glu Phe Arg Pro Lys
210 215 220

```
Ile Lys Gly Glu His Pro Gly Leu Ser Ile Gly Asp Val Ala Lys Lys
225                 230                 235                 240

Leu Gly Glu Met Trp Asn Asn Thr Ala Ala Asp Asp Lys Gln Pro Tyr
                245                 250                 255

Glu Lys Lys Ala Ala Lys Leu Lys Glu Lys Tyr Glu Lys Asp Ile Ala
            260                 265                 270

Ala Tyr Arg Ala Lys Gly Lys Val Asp Ala Gly Lys Lys Val Val Ala
        275                 280                 285

Lys Ala Glu Lys Ser Lys Lys Lys Glu Glu Glu Asp
            290                 295                 300

<210> SEQ ID NO 21
<211> LENGTH: 111
<212> TYPE: PRT
<213> ORGANISM: Artificial sequence
<220> FEATURE:
<223> OTHER INFORMATION: Synthetic peptide: BS/AI/CD154

<400> SEQUENCE: 21

Ser Ser Ser Thr Tyr Gln Arg Thr Arg Ala Leu Val Arg Thr Gly Met
1               5                   10                  15

Asp Ser Ser Ala Asn Pro Ala Asn Asp Leu Cys Tyr Pro Gly Asp
            20                  25                  30

Phe Asn Asp Tyr Glu Glu Leu Ser Ser Gly Arg Leu Ile Gln Asn
        35                  40                  45

Ser Ile Thr Ile Glu Arg Met Val Leu Ser Ser Ser Leu Leu Ser
    50                  55                  60

Arg Ile Asn His Phe Glu Lys Ile Gln Ser Ser Ser Glu Val Glu Thr
65                  70                  75                  80

Pro Ile Arg Asn Ser Ser Ser Glu Val Glu Thr Pro Thr Arg Asn Ser
                85                  90                  95

Ser Ser Trp Met Thr Thr Ser Tyr Ala Pro Thr Ser Ser Ser Ser
            100                 105                 110

<210> SEQ ID NO 22
<211> LENGTH: 290
<212> TYPE: PRT
<213> ORGANISM: Artificial sequence
<220> FEATURE:
<223> OTHER INFORMATION: Synthetic peptide: BS/AI/HMGB1

<400> SEQUENCE: 22

Ser Ser Ser Thr Tyr Gln Arg Thr Arg Ala Leu Val Arg Thr Gly Met
1               5                   10                  15

Asp Ser Ser Ala Asn Pro Ala Asn Asp Leu Cys Tyr Pro Gly Asp
            20                  25                  30

Phe Asn Asp Tyr Glu Glu Leu Ser Ser Gly Arg Leu Ile Gln Asn
        35                  40                  45

Ser Ile Thr Ile Glu Arg Met Val Leu Ser Ser Ser Leu Leu Ser
    50                  55                  60

Arg Ile Asn His Phe Glu Lys Ile Gln Ser Ser Ser Glu Val Glu Thr
65                  70                  75                  80

Pro Ile Arg Asn Ser Ser Ser Glu Val Glu Thr Pro Thr Arg Asn Ser
                85                  90                  95

Ser Ser Ser Ser Met Gly Lys Gly Asp Pro Lys Lys Pro Arg Gly Lys
            100                 105                 110

Met Ser Ser Tyr Ala Phe Phe Val Gln Thr Cys Arg Glu Glu His Lys
        115                 120                 125
```

```
Lys Lys His Pro Asp Ala Ser Val Asn Phe Ser Glu Phe Ser Lys Lys
    130                 135                 140
Cys Ser Glu Arg Trp Lys Thr Met Ser Ser Lys Glu Lys Gly Lys Phe
145                 150                 155                 160
Glu Asp Met Ala Lys Ala Asp Lys Leu Arg Tyr Glu Lys Glu Met Lys
                165                 170                 175
Asn Tyr Val Pro Pro Lys Gly Glu Thr Lys Lys Phe Lys Asp Pro
            180                 185                 190
Asn Ala Pro Lys Arg Pro Pro Ser Ala Phe Phe Leu Phe Cys Ser Glu
            195                 200                 205
Phe Arg Pro Lys Ile Lys Gly Glu His Pro Gly Leu Ser Ile Gly Asp
    210                 215                 220
Val Ala Lys Lys Leu Gly Glu Met Trp Asn Asn Thr Ala Ala Asp Asp
225                 230                 235                 240
Lys Gln Pro Tyr Glu Lys Lys Ala Ala Lys Leu Lys Glu Lys Tyr Glu
                245                 250                 255
Lys Asp Ile Ala Ala Tyr Arg Ala Lys Gly Lys Val Asp Ala Gly Lys
                260                 265                 270
Lys Val Val Ala Lys Ala Glu Lys Ser Lys Lys Lys Glu Glu
            275                 280                 285
Glu Asp
    290

<210> SEQ ID NO 23
<211> LENGTH: 85
<212> TYPE: PRT
<213> ORGANISM: Artificial sequence
<220> FEATURE:
<223> OTHER INFORMATION: Synthetic peptide: HMGB1 box a1

<400> SEQUENCE: 23

Met Gly Lys Gly Asp Pro Lys Lys Pro Arg Gly Lys Met Ser Ser Tyr
1               5                   10                  15
Ala Phe Phe Val Gln Thr Cys Arg Glu Glu His Lys Lys Lys His Pro
                20                  25                  30
Asp Ala Ser Val Asn Phe Ser Glu Phe Ser Lys Lys Cys Ser Glu Arg
            35                  40                  45
Trp Lys Thr Met Ser Ser Lys Glu Lys Gly Lys Phe Glu Asp Met Ala
    50                  55                  60
Lys Ala Asp Lys Leu Arg Tyr Glu Lys Glu Met Lys Asn Tyr Val Pro
65                  70                  75                  80
Pro Lys Gly Glu Thr
                85

<210> SEQ ID NO 24
<211> LENGTH: 54
<212> TYPE: PRT
<213> ORGANISM: Artificial sequence
<220> FEATURE:
<223> OTHER INFORMATION: Synthetic peptide: HMGB1 box a2

<400> SEQUENCE: 24

Pro Asp Ala Ser Val Asn Phe Ser Glu Phe Ser Lys Lys Cys Ser Glu
1               5                   10                  15
Arg Trp Lys Thr Met Ser Ser Lys Glu Lys Gly Lys Phe Glu Asp Met
                20                  25                  30
```

Ala Lys Ala Asp Lys Leu Arg Tyr Glu Lys Glu Met Lys Asn Tyr Val
            35                  40                  45

Pro Pro Lys Gly Glu Thr
    50

<210> SEQ ID NO 25
<211> LENGTH: 73
<212> TYPE: PRT
<213> ORGANISM: Artificial sequence
<220> FEATURE:
<223> OTHER INFORMATION: Synthetic peptide: HMGB1 box b1

<400> SEQUENCE: 25

Lys Asp Pro Asn Ala Pro Lys Arg Pro Pro Ser Ala Phe Phe Leu Phe
1               5                   10                  15

Cys Ser Glu Phe Arg Pro Lys Ile Lys Gly Glu His Pro Gly Leu Ser
            20                  25                  30

Ile Gly Asp Val Ala Lys Lys Leu Gly Glu Met Trp Asn Asn Thr Ala
        35                  40                  45

Ala Asp Asp Lys Gln Pro Tyr Glu Lys Lys Ala Ala Lys Leu Lys Glu
    50                  55                  60

Lys Tyr Glu Lys Asp Ile Ala Ala Tyr
65                  70

<210> SEQ ID NO 26
<211> LENGTH: 69
<212> TYPE: PRT
<213> ORGANISM: Artificial sequence
<220> FEATURE:
<223> OTHER INFORMATION: Synthetic peptide: HMGB1 box b2

<400> SEQUENCE: 26

Asn Ala Pro Lys Arg Pro Pro Ser Ala Phe Phe Leu Phe Cys Ser Glu
1               5                   10                  15

Phe Arg Pro Lys Ile Lys Gly Glu His Pro Gly Leu Ser Ile Gly Asp
            20                  25                  30

Val Ala Lys Lys Leu Gly Glu Met Trp Asn Asn Thr Ala Ala Asp Asp
        35                  40                  45

Lys Gln Pro Tyr Glu Lys Lys Ala Ala Lys Leu Lys Glu Lys Tyr Glu
    50                  55                  60

Lys Asp Ile Ala Ala
65

<210> SEQ ID NO 27
<211> LENGTH: 21
<212> TYPE: PRT
<213> ORGANISM: Artificial sequence
<220> FEATURE:
<223> OTHER INFORMATION: Synthetic peptide: HMGB1 RAGE Binding domain

<400> SEQUENCE: 27

Lys Asp Pro Asn Ala Pro Lys Arg Pro Pro Ser Ala Phe Phe Leu Phe
1               5                   10                  15

Cys Ser Glu Phe Arg
            20

<210> SEQ ID NO 28
<211> LENGTH: 33
<212> TYPE: PRT
<213> ORGANISM: Artificial sequence

```
<220> FEATURE:
<223> OTHER INFORMATION: Synthetic peptide: HMGB1 proinflammatory
      cytokine activity

<400> SEQUENCE: 28

Leu Lys Glu Lys Tyr Glu Lys Asp Ile Ala Ala Tyr Arg Ala Lys Gly
1               5                   10                  15

Lys Val Asp Ala Gly Lys Lys Val Val Ala Lys Ala Glu Lys Ser Lys
            20                  25                  30

Lys

<210> SEQ ID NO 29
<211> LENGTH: 215
<212> TYPE: PRT
<213> ORGANISM: Homo sapiens
<220> FEATURE:
<221> NAME/KEY: misc_feature
<223> OTHER INFORMATION: HMGB1

<400> SEQUENCE: 29

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Lys Glu Glu Glu Asp Glu Glu
            180                 185                 190

Asp Glu Glu Asp Glu Glu Glu Glu Asp Glu Glu Asp Glu Asp Glu Glu
        195                 200                 205

Glu Glu Asp Asp Asp Asp Glu
    210                 215

<210> SEQ ID NO 30
<211> LENGTH: 205
<212> TYPE: PRT
<213> ORGANISM: Danio rerio
<220> FEATURE:
<221> NAME/KEY: misc_feature
<223> OTHER INFORMATION: Zebra fish HMGB1
```

<400> SEQUENCE: 30

```
Met Gly Lys Asp Pro Thr Lys Pro Arg Gly Lys Met Ser Ser Tyr Ala
1               5                   10                  15

Tyr Phe Val Gln Thr Cys Arg Glu Glu His Lys Lys His Pro Glu
            20                  25                  30

Ala Thr Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
50                  55                  60

Leu Asp Lys Ala Arg Tyr Glu Arg Glu Met Lys Asn Tyr Ile Pro Pro
65                  70                  75                  80

Lys Gly Glu Lys Lys Arg Phe Lys Asp Pro Asn Ala Pro Lys Arg
                85                  90                  95

Pro Pro Ser Ala Phe Phe Ile Phe Cys Ser Glu Phe Arg Pro Lys Val
            100                 105                 110

Lys Glu Glu Thr Pro Gly Leu Ser Ile Gly Asp Val Ala Lys Arg Leu
            115                 120                 125

Gly Glu Met Trp Asn Lys Ile Ser Ser Glu Lys Gln Pro Tyr Glu
130                 135                 140

Lys Lys Ala Ala Lys Leu Lys Glu Lys Tyr Glu Lys Asp Ile Ala Ala
145                 150                 155                 160

Tyr Arg Ser Lys Gly Lys Val Gly Gly Gly Ala Lys Ala Pro Ser
                165                 170                 175

Lys Pro Asp Lys Ala Asn Asp Glu Asp Glu Asp Asp Glu Glu Glu
            180                 185                 190

Asp Glu Asp Asp Asp Asp Glu Glu Glu Asp Glu
            195                 200                 205
```

<210> SEQ ID NO 31
<211> LENGTH: 53
<212> TYPE: DNA
<213> ORGANISM: Artificial sequence
<220> FEATURE:
<223> OTHER INFORMATION: Synthetic primer: mazF for - MazF gene

<400> SEQUENCE: 31
ctaaaatctt cagatgatca atcatcctca ctgcccgctt tccagtcggg aaa    53

<210> SEQ ID NO 32
<211> LENGTH: 44
<212> TYPE: DNA
<213> ORGANISM: Artificial sequence
<220> FEATURE:
<223> OTHER INFORMATION: Synthetic primer: mazF rev - MazF gene

<400> SEQUENCE: 32
tgaacgtgac gaacgaccag atttcccct atgcaagggt ttat    44

<210> SEQ ID NO 33
<211> LENGTH: 20
<212> TYPE: DNA
<213> ORGANISM: Artificial sequence
<220> FEATURE:
<223> OTHER INFORMATION: Synthetic primer: CotB up for - Cot B up

<400> SEQUENCE: 33
gaaatgctcg atgctgatga    20

```
<210> SEQ ID NO 34
<211> LENGTH: 27
<212> TYPE: DNA
<213> ORGANISM: Artificial sequence
<220> FEATURE:
<223> OTHER INFORMATION: Synthetic primer: Cot B up rev - Cot B up

<400> SEQUENCE: 34
ggatgattga tcatctgaag attttag                                           27

<210> SEQ ID NO 35
<211> LENGTH: 24
<212> TYPE: DNA
<213> ORGANISM: Artificial sequence
<220> FEATURE:
<223> OTHER INFORMATION: Synthetic primer: Cot B dn for - Cot B down

<400> SEQUENCE: 35
aaatctggtc gttcgtcacg ttca                                              24

<210> SEQ ID NO 36
<211> LENGTH: 25
<212> TYPE: DNA
<213> ORGANISM: Artificial sequence
<220> FEATURE:
<223> OTHER INFORMATION: Synthetic primer: Cot B dn rev - Cot B down

<400> SEQUENCE: 36
ttacgtttcc agtgatagtc tatcg                                             25

<210> SEQ ID NO 37
<211> LENGTH: 186
<212> TYPE: DNA
<213> ORGANISM: Artificial sequence
<220> FEATURE:
<223> OTHER INFORMATION: Synthetic primer: BS/AI/HMGB1 for - BS/AI/HMGB1
      CotB up

<400> SEQUENCE: 37
aaccattctt tcaattgtaa ttgaattttg aatcagtctg cctgatgatg acagttcttc       60
ataatcatta aaatcgcccg gatagcacag atcatttgcc ggatttgctg atgatgaatc      120
catgcctgtt ctaaccagtg ctcttgttct ttgatatgtg gatgattgat catctgaaga      180
ttttag                                                                 186

<210> SEQ ID NO 38
<211> LENGTH: 200
<212> TYPE: DNA
<213> ORGANISM: Artificial sequence
<220> FEATURE:
<223> OTHER INFORMATION: Synthetic primer: BS/AI/HMGB1 rev - BS/AI/HMGB1
      CotB down

<400> SEQUENCE: 38
ttacaattga agaatggtt ctgtcatcat catcactgct gtcaagaatt aatcattttg        60
aaaaaattca atcatcatca gaagttgaaa caccgattag aaattcatca tcatggatga     120
caacatcata tgcaccgaca tcatcatcat cagaagttga acaccgatt agaaataaat     180 ctggtcgttc gtcacgttca                                                  200

<210> SEQ ID NO 39
<211> LENGTH: 177
<212> TYPE: DNA
<213> ORGANISM: Artificial sequence
```

-continued

<220> FEATURE:
<223> OTHER INFORMATION: Synthetic primer: BS/AI/CD154 for - BS/AI/CD154 CotB up

<400> SEQUENCE: 39

```
ttcaaaatga ttaattcttg acagcagtga tgatgatgac agaaccattc tttcaattgt     60
aattgaattt tgaatcagtc tgcctgatga tgacagttct tcataatcat taaaatcgcc    120
cggatagcac agatcatttg ccggatttgc ggatgattga tcatctgaag attttag      177
```

<210> SEQ ID NO 40
<211> LENGTH: 194
<212> TYPE: DNA
<213> ORGANISM: Artificial sequence
<220> FEATURE:
<223> OTHER INFORMATION: Synthetic primer: BS/AI/CD154 rev - BS/AI/CD154 CotB down

<400> SEQUENCE: 40

```
caagaattaa tcattttgaa aaaattcaat catcatcaga agttgaaaca ccgattagaa     60
attcatcatc actgaaagaa aaatatgaaa aagatattgc agcatataga gcaaaaggca    120
aagttgatgc aggcaaaaaa gttgttgcaa aagcagaaaa atcaaaaaaa aaatctggtc    180
gttcgtcacg ttca                                                      194
```

VACCINE VECTORS AND METHODS OF ENHANCING IMMUNE RESPONSES

CROSS-REFERENCE TO RELATED APPLICATIONS

This patent application is a Continuation of U.S. patent application Ser. No. 13/574,504, filed Jul. 20, 2012 and issuing Feb. 17, 2015 as U.S. Pat. No. 8,956,618, which is a national stage filing under 35 U.S.C. 371 of International Application No. PCT/US2011/022062, filed Jan. 21, 2011, which claims the benefit of priority of U.S. Provisional Patent Application No. 61/297,098, filed Jan. 21, 2010, all of which are incorporated herein by reference their entirety.

INTRODUCTION

Vaccines are used to initiate an adaptive immune response against antigens, in particular antigens from pathogens, tumor cells or the like, in order to ameliorate or prevent disease. Synthetic peptides or killed or attenuated microorganism vaccines are often effective at stimulating a robust immune response that is fully protective. In some cases these vaccines are not protective or only partially protective and other strategies must be used to develop protective vaccines. Attenuated microorganism based vaccines also are associated with risks of gene transfer or mutation repair and may pose risks to immunocompromised individuals. Development of new vaccines that are safe and effective at stimulating lasting protective immune responses is needed.

Influenza virus infection, particularly avian influenza H5N1, presents a mounting health and economic concern. Evidence clearly indicates that H5N1 is continuing to circulate between susceptible birds and swine in widening regions of the world. Many scientists believe that if left unchecked, the current H5N1 avian influenza will mutate to allow for human to human transmission and cause a worldwide pandemic. With a mortality rate of over 50%, such an outbreak would be devastating. Regardless of the ability of the virus to cause human disease, avian influenza H5N1 is already threatening to have a huge economic impact due to the eradication of poultry flocks in affected areas. Therefore, development of a vaccine to protect humans, poultry, swine and other domesticated animals from H5N1 influenza is needed. An influenza vaccine that is capable of protecting against 1H5N1 as well as other influenza viruses, such as H1N1, would be optimal.

SUMMARY

Vaccine vectors and methods of stimulating an immune response and methods of reducing morbidity associated with Influenza infection are provided herein. In one aspect, a vaccine vector including an antigenic polypeptide and an HMGB1 polypeptide or a functional fragment thereof is provided. At least a portion of the antigenic polypeptide and the HMGB1 polypeptide are present on the surface of the vaccine vector. The vaccine vector may include a first polynucleotide encoding the antigenic polypeptide and a second polynucleotide encoding the HMGB1 polypeptide. The HMGB1 polypeptide and the antigenic polypeptide may be linked, such as in a fusion protein. The HMGB1 polypeptide and the antigenic polypeptide may both be inserted within an external loop of a transmembrane protein.

In another aspect, a composition comprising the vaccine vector and a pharmaceutically acceptable carrier is provided. The pharmaceutically acceptable carrier may be acceptable for oral or nasal use. The vaccine vector may be incapable of replication.

In yet another aspect, a *Bacillus* spp. vaccine vector is provided. The vaccine vector includes a first polynucleotide sequence encoding an antigenic polypeptide expressed on the surface of the vaccine vector and a second polynucleotide sequence encoding an immunostimulatory polypeptide expressed on the surface of the vaccine vector. The antigenic polypeptide may be an Influenza M2e polypeptide, an Influenza HA polypeptide, or an Influenza NP polypeptide or a combination thereof. The immunostimulatory polypeptide may be a CD154 polypeptide or a HMGB1 polypeptide or a combination thereof. The immunostimulatory polypeptide and the antigenic polypeptide may be linked, such as in a fusion protein and may be inserted with an external loop of a transmembrane protein.

In still another aspect, methods of enhancing an immune response in a subject are provided. In the method, the vaccine vectors or compositions provided herein are administered to the subject in an amount effective to enhance the immune response of the subject to the antigenic polypeptide. Suitably, the vaccine vector is administered orally or intranasally.

In a further aspect, methods of enhancing the immune response in a subject by administering a *Bacillus* spp. vaccine vector as described herein are provided. The vaccine vector includes a first polynucleotide sequence encoding an antigenic polypeptide expressed on the surface of the vaccine vector and a second polynucleotide sequence encoding an immunostimulatory polypeptide expressed on the surface of the vaccine vector. The antigenic polypeptide may be an Influenza M2e polypeptide, an Influenza HA polypeptide, an Influenza NP polypeptide or a combination thereof. The immunostimulatory polypeptide may be a CD154 polypeptide, a HMGB1 polypeptide or a combination thereof.

In a still further aspect, methods of reducing influenza related morbidity in a subject are provided. In the methods, administration of the vaccine vectors or compositions disclosed herein reduces the morbidity associated with a subsequent influenza infection.

BRIEF DESCRIPTION OF THE FIGURES

FIG. 4 is a graph showing the S/P ratios of the ELISA for M2e specific antibody production by chickens after oral gavage of the indicated dosage of live or variously inactivated *Bacillus subtilis* vaccine vectors expressing the Influenza A epitopes and either HMGB1 or CD154 as compared to chickens vaccinated with the *Bacillus* vector alone (BSBB).

FIG. 5 is a graph showing the S/P ratios of the ELISA for HA LB specific antibody production by chickens after oral gavage of the indicated dosage of live or variously inactivated *Bacillus subtilis* vaccine vectors expressing the Influenza A epitopes and either HMGB1 or CD154 as compared to chickens vaccinated with the *Bacillus* vector alone (BSBB).

FIG. 7 is a graph showing the S/P ratios of the ELISA for M2e specific IgG antibody production by chickens after oral gavage of either $10^6$ live or the various indicated dosages of formalin inactivated *Bacillus subtilis* vaccine vectors expressing the Influenza A epitopes and HMGB1 as compared to chickens vaccinated with the *Bacillus* vector alone (BSBB).

FIG. 9 is a graph showing the S/P ratios of the ELISA for M2e specific IgA antibody production by chickens vaccinated, either orally or subcutaneously, with $10^6$ live, formalin inactivated or formalin inactivated and lyophilized *Bacillus subtilis* vaccine vectors expressing the Influenza A epitopes and HMGB1 as compared to chickens vaccinated with the *Bacillus* vector alone (BSBB).

DETAILED DESCRIPTION

Figure 1:
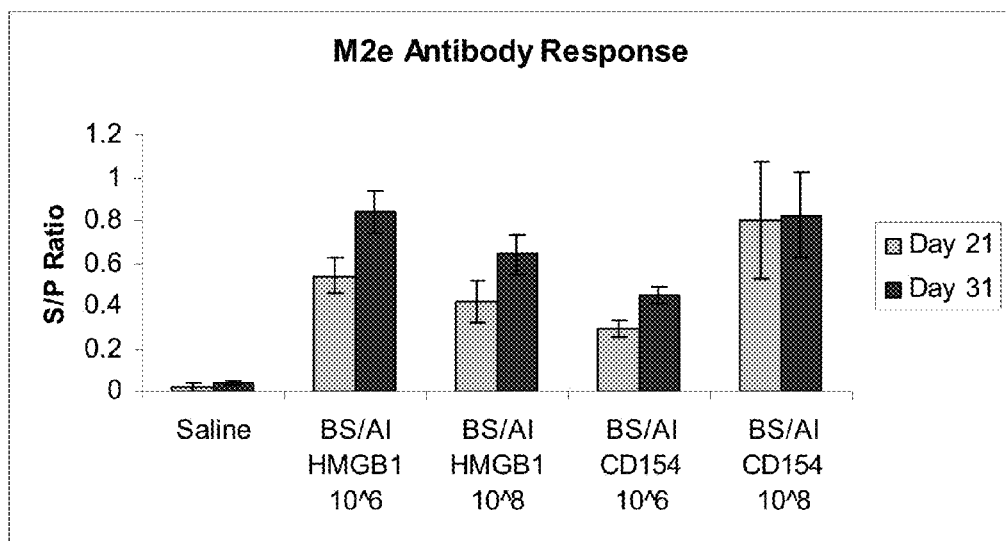
FIG. 1 is a graph showing the S/P (sample to positive control) ratios of the ELISA for M2e specific antibody production by chickens after oral gavage of the indicated dosage of *Bacillus subtilis* vaccine vector expressing the Influenza A epitopes and either HMGB1 or CD154 as compared to chickens vaccinated with saline.

Recombinant DNA technologies enable relatively easy manipulation of many bacterial and viral species. Some bacteria and viruses are either naturally or can be selected or engineered to be mildly pathogenic or non-pathogenic, but remain capable of generating a robust immune response. These bacteria and viruses make attractive vaccine vectors for eliciting an immune response to heterologous or foreign antigens. Bacterial or viral vaccine vectors may mimic the natural infection and produce robust and long lasting immunity. Vaccine vectors are often relatively inexpensive to produce and administer. In addition, such vectors can often carry more than one antigen and may provide protection against multiple infectious agents.

Live bacterial or viral vaccine vectors may still pose risks to immunocompromised individuals and require additional regulatory scrutiny. Thus use of vectors that are killed or inactivated or qualify as Generally Regarded As Safe (GRAS) organisms by the Food and Drug Administration (FDA) is desirable. The problem is generating a robust immune response using such vectors. As shown in the Examples, by including HMGB1 (high mobility group box 1) polypeptides on the surface of the vaccine vector we can generate a robust immune response against antigenic polypeptides using a *Bacillus* spp. vector. In fact, the Examples demonstrate that this vector can be inactivated such that it cannot replicate using a variety of methods and still elicit a robust immune response after administration.

Vaccine vectors including an antigenic polypeptide and an HMGB1 polypeptide or a functional fragment thereof are provided herein. At least a portion of the antigenic polypeptide and at least a portion of the HMGB1 polypeptide or functional fragment thereof are present on the surface of the vaccine vector. The vaccine vector may include a first polynucleotide encoding the antigenic polypeptide and a second polynucleotide encoding the HMGB1 polypeptide. The HMGB1 polypeptide and the antigenic polypeptide may be linked, such as in a fusion protein or may be expressed separately. The HMGB1 polypeptide and the antigenic polypeptide may both be inserted within an external loop of a transmembrane protein.

The vaccine vectors may be bacterial, viral or liposome-based vectors. Potential vaccine vectors include, but are not limited to, *Bacillus* (*Bacillus subtilis*), *Salmonella* (*Salmonella enteritidis*), *Shigella*, *Escherichia* (*E. coli*), *Yersinia*, *Bordetella*, *Lactococcus*, *Streptococcus*, *Vibrio* (*Vibrio cholerae*), *Listeria*, adenovirus, poxvirus, herpesvirus, alphavirus, and adeno-associated virus. Suitably, the vaccine vector is a GRAS organism. The vaccine vector may be inactivated or killed such that it is not capable of replicating. Methods of inactivating or killing bacterial or viral vaccine vectors are known to those of skill in the art and include, but are not limited to methods such as those shown in the Examples, namely formalin inactivation, antibiotic-based inactivation, heat treatment and ethanol treatment.

An antigenic polypeptide is a polypeptide that is capable of being specifically recognized by the adaptive immune system. An antigenic polypeptide includes any polypeptide that is immunogenic. The antigenic polypeptides include, but are not limited to, antigens that are pathogen-related, allergen-related, tumor-related or disease-related. Pathogens include viral, parasitic, fungal and bacterial pathogens as well as protein pathogens such as the prions. The antigenic polypeptides may be full-length proteins or portions thereof. It is well established that immune system recognition of many proteins is based on a relatively small number of amino acids, often referred to as the epitope. Epitopes may be only 8-10 amino acids. Thus, the antigenic polypeptides described herein may be full-length proteins, 8 amino acid long epitopes or any portion between these extremes. In fact the antigenic polypeptide may include more than one epitope from a single pathogen or protein.

Multiple copies of the same epitope or multiple epitopes from different proteins may be included in the vaccine vector. It is envisioned that several epitopes or antigens from the same or different pathogens or diseases may be administered in combination in a single vaccine vector to generate an enhanced immune response against multiple antigens. Recombinant vaccine vectors may encode antigens from multiple pathogenic microorganisms, viruses or tumor associated antigens. Administration of vaccine vectors capable of expressing multiple antigens has the advantage of inducing immunity against two or more diseases at the same time.

The antigenic polypeptide may be an Influenza polypeptide, suitably it is an Influenza H5N1 polypeptide or a polypeptide associated with multiple strains of the Influenza virus such as a polypeptide of the Influenza M2 protein. The ectodomain of the Influenza A virus M2 protein, known as M2e, protrudes from the surface of the virus. The M2e portion of the M2 protein contains about 24 amino acids. The M2e polypeptide varies little from one isolate to the next within Influenza. In fact, only a few naturally occurring mutations in M2e have been isolated from infected humans since the 1918 flu epidemic. In addition, influenza viruses isolated from avian and swine hosts have different, yet still conserved, M2e sequences. For reviews of the M2e polypeptide sequences isolated from human, avian and swine hosts see Liu et al., Microbes and Infection 7:171-177 (2005) and Reid et al., J. Virol. 76:10717-10723 (2002) each of which are incorporated herein by reference in its entirety. See also SEQ ID NO: 1-4.

Suitably the entire M2e polypeptide may be inserted into the vaccine vector or only a portion may be used. In the Examples, an eight amino acid polypeptide (LM2 having amino acid sequence: EVETPIRN, SEQ ID NO:5 or its variant M2eA having amino acid sequence EVETPTRN, SEQ ID NO:6) was incorporated into the vaccine vector and demonstrated to produce an antibody response after administration to chickens. Suitably, the portion of the M2e polypeptide inserted into the vaccine vector is immunogenic. An immunogenic fragment is a peptide or polypeptide capable of eliciting a cellular or humoral immune response. Suitably, an immunogenic fragment of M2e may be the full-length M2e polypeptide, or suitably may be 20 or more amino acids, 15 or more amino acids, 10 or more amino acids or 8 or more amino acids of the full-length sequence.

Other suitable epitopes for inclusion in an Influenza A vaccine vector include, but are not limited to, polypeptides of the hemagglutinin (HA) or the nuclear protein (NP) of Influenza A. For example, the peptides of SEQ ID NO:7, SEQ ID NO:8, SEQ ID NO:9, or SEQ ID NO:10 may be included in a vaccine vector. In the Examples, SEQ ID NO: 7 (HAUA) and SEQ ID NO: 8 (HALB) were incorporated into the vaccine vector and demonstrated to produce an antibody response after administration to chickens. See FIGS. 2-3 and 5-6. In addition, the NP epitopes of SEQ ID NO: 9 (NP54) and SEQ ID NO: 10 (NP147) were incorporated into the vaccine vector in the examples. One of skill in the art will appreciate that any of these sequences may be used in combination with any other epitope including epitopes derived from other pathogens or antigens.

The HMGB1 (High Mobility Group Box-1) protein was first identified as a DNA-binding protein critical for DNA structure and stability. It is a ubiquitously expressed nuclear protein that binds DNA with no sequence specificity. The protein is highly conserved and found in plants to mammals. The zebrafish, chicken and human HMGB1 amino acid sequences are provided in SEQ ID NO: 30, SEQ ID NO: 18 and SEQ ID NO: 29, respectively. The sequence throughout mammals is highly conserved with 98% amino acid identity and the amino acid changes are conservative. Thus an HMGB1 protein from one species can likely substitute for that from another species functionally. The full-length HMGB1 protein or a portion thereof may be used as the HMGB1 polypeptide in the vaccine vectors described herein. HMGB1 has two DNA binding regions termed A box as shown in SEQ ID NO: 23 and 24 and B box as shown in SEQ ID NO: 25 and 26. See Andersson and Tracey, Annu. Rev. Immunol. 2011, 29:139-162, which is incorporated herein by reference in its entirety.

HMGB1 is a mediator of inflammation and serves as a signal of nuclear damage, such as from necrotic cells. HMGB1 can also be actively secreted by cells of the monocyte/macrophage lineage in a process requiring acetylation of the protein, translocation across the nucleus and secretion. Extracellular HMGB1 acts as a potent mediator of inflammation by signaling via the Receptor for Advanced Glycated End-products (RAGE) and via members of the Toll-like Receptor family (TLR), in particular TLR4. The RAGE binding activity has been identified and requires the polypeptide of SEQ ID NO: 27. TLR4 binding requires the cysteine at position 106 of SEQ ID NO: 18, which is found in the B box region of HMGB1.

The inflammatory activities of HMGB1 do not require the full-length protein and functional fragments have been identified. The B box has been shown to be sufficient to mediate the pro-inflammatory effects of HMGB1 and thus SEQ ID NO: 25 and 26 are HMGB1 polypeptides or functional fragments thereof within the context of the present invention. In addition, the RAGE binding site and the pro-inflammatory cytokine activity have been mapped to SEQ ID NO: 27 and SEQ ID NO: 28, respectively. Thus, these polypeptides are functional fragments of HMGB1 polypeptides in the context of the present invention.

Those of skill in the art are capable of identifying HMGB1 polypeptides and fragments thereof capable of stimulating pro-inflammatory cytokine activity, using methods such as those in International Publication No. WO02 092004, which is incorporated herein by reference in its entirety. Suitably, the HMGB1 polypeptide includes the RAGE binding domain at amino acids 150-183 of SEQ ID NO:18 (SEQ ID NO: 27 or a homolog thereof) and the pro-inflammatory cytokine activity domain between amino acids 89-109 of SEQ ID NO: 18 (SEQ ID NO: 28 or a homolog thereof). In particular, HMGB1 polypeptides and functional fragments or homologs thereof include polypeptides identical to, or at least 99% identical, at least 98% identical, at least 95% identical, at least 90% identical, at least 85% identical, or at least 80% identical to the HMGB1 polypeptides of SEQ ID NOs: 18 or 23-30.

At least a portion of the antigenic polypeptide and at least a portion of the HMGB1 polypeptide are present on the surface of the vaccine vector. Present on the surface of the vaccine vector includes polypeptides that are comprised within a transmembrane protein, interacting with, covalently or chemically cross-linked to a transmembrane protein, a membrane lipid or membrane anchored carbohydrate. A polypeptide can be comprised within a transmembrane protein by having the amino acids comprising the polypeptide linked via a peptide bond to the N-terminus, C-terminus or anywhere within the transmembrane protein (i.e. inserted between two amino acids of the transmembrane protein or in place of one or more amino acids of the transmembrane protein (i.e. deletion-insertion). Suitably, the polypeptides may be inserted into an external loop of a transmembrane protein. Suitable transmembrane proteins are cotB and lamB, but those of skill in the art will appreciate many suitable transmembrane proteins are available.

Alternatively, the polypeptides may be covalently or chemically linked to proteins, lipids or carbohydrates in the membrane, or capsid if a viral vector is being used through methods available to persons of skill in the art. For example, di-sulfide bonds or biotin-avidin cross-linking could be used to present the antigenic and HMGB1 polypeptides on the surface of a vaccine vector. Suitably, the antigenic polypeptide and the HMGB1 polypeptide are part of a fusion protein. The two polypeptides may be directly linked via a peptide bond or may be separated by a linker or a section of a third protein into which they are inserted.

Polynucleotides encoding the antigenic polypeptide or HMGB1 polypeptide may be inserted into the vaccine vector and expressed to generate the antigenic polypeptide and the HMGB1 polypeptide. The polynucleotides may be inserted into the chromosome of the vaccine vector or encoded on plasmids or other extrachromosomal DNA. Suitably, polynucleotides encoding the antigenic polypeptide and/or the HMGB1 polypeptide may be expressed independently or are inserted into a vaccine vector polynucleotide that is expressed. Suitably, the vaccine vector polynucleotide encodes a polypeptide expressed on the surface of the vaccine vector such as a transmembrane protein. The polynucleotide encoding the antigenic polypeptide and/or the HMGB1 polypeptide may be inserted into the vaccine vector polynucleotide sequence to allow expression of the antigenic polypeptide and/or the HMGB1 polypeptide on the surface of the vector. For example, the polynucleotide encoding the antigenic polypeptide and the HMGB1 polypeptide may be inserted in frame into a bacterial polynucleotide in a region encoding an external loop region of a transmembrane protein such that the bacterial polynucleotide sequence remains in frame. See Example 1.

Alternatively, the polynucleotide encoding the antigenic polypeptide and/or the HMGB1 polypeptide may be inserted into a secreted polypeptide which is displayed or presented on the surface of the vaccine vector through association with a protein, lipid or carbohydrate on the surface of the vaccine vector. Those of skill in the art will appreciate that the polynucleotide encoding the antigenic polypeptide and/or the HMGB1 polypeptide could be inserted in a wide variety of vaccine vector polynucleotides to provide expression and presentation of the antigenic polypeptide and/or the HMGB1 polypeptide to the immune cells of a subject treated with the vaccine vector. In the Examples, several Influenza epitopes including an M2e epitope, a HA epitope and a NP epitope were expressed from a plasmid for vegetative expression in *Bacillus subtilis*. The resulting recombinant bacteria express the inserted epitopes as demonstrated by the immune response shown in FIGS. 1-6.

In the Examples, the vaccine vectors have the antigenic polypeptides (M2e, HA and NP polypeptides) and the immunostimulatory polypeptide (either CD154 or HMGB1) encoded on the same polynucleotide and in frame with each other. In alternative embodiments, the immunostimulatory polypeptide and the antigenic polypeptide may be encoded by distinct polynucleotides. Those of skill in the art will appreciate that a variety of methods may be used to obtain expression of the antigenic polypeptide and the HMGB1 polypeptide on the surface of the vaccine vector. Such methods are known to those skilled in the art.

Compositions comprising the vaccine vector and a pharmaceutically acceptable carrier are also provided. A pharmaceutically acceptable carrier is any carrier suitable for in vivo administration. Suitably, the pharmaceutically acceptable carrier is acceptable for oral, nasal or mucosal delivery. The pharmaceutically acceptable carrier may include water, buffered solutions, glucose solutions or bacterial culture fluids. Additional components of the compositions may suitably include excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying. The vaccine vector in the compositions may not be capable of replication, suitably the vaccine vector is inactivated or killed prior to addition to the composition.

The compositions described herein may be used to enhance an immune response such as an antibody response to the antigenic polypeptide. The compositions containing Influenza polypeptides may also be used to decrease the morbidity associated with subsequent Influenza infection. The compositions may prevent Influenza from causing disease or any associated morbidity in a subject to which the compositions or vaccine vectors described herein were administered. The compositions and vaccine vectors described herein may reduce the severity of subsequent disease by decreasing the length of disease, decreasing the morbidity or mortality associated with the disease or reducing the likelihood of contracting the disease. The morbidity or mortality associated with the disease after administration of the vaccine vectors described herein may be reduced by 25%, 30%, 40%, 50%, 60%, 70%, 80%, 90% or even 100% as compared to similar subjects not provided the vaccine vector.

Methods of enhancing immune responses in a subject by administering a vaccine vector are also provided. The vaccine vector may contain a HMGB1 polypeptide capable of stimulating the immune response to the vaccine vector and its associated antigenic polypeptide. The vaccine vector comprising a polypeptide of HMGB1 is administered to a subject in an amount effective to enhance the immune response of the subject to the vaccine and in particular to the antigenic polypeptide. Suitably, the vaccine vector contains a polynucleotide encoding a polypeptide including amino acids 150-183 and 89-109 of the HMGB1 polypeptide (SEQ ID NO: 18) or a homolog thereof. In the Examples, a 190 amino acid polypeptide of HMGB1 was used. Suitably, the polynucleotide encodes a HMGB1 polypeptide from the same species as the subject. Heterologous combinations of HMGB1 polypeptides and subjects (i.e. a human HMGB1 polypeptide for use in a chicken vaccine) may be useful in the methods of the invention because HMGB1 is highly conserved through a wide number of species. The HMGB1 polypeptide may be used to enhance the immune response in the subject to any foreign antigen or antigenic polypeptide present in or on the vaccine vector. One of skill in the art will appreciate that the HMGB1 polypeptide could be used to enhance the immune response to more than one antigenic polypeptide present in a vaccine vector. The polypeptide from HMGB1 stimulates an immune response at least in part by activating dendritic cells and macrophages and thus stimulating production of cytokines such as IL-1, IL-6, IFN-γ and TNF-α. In the Examples, a polypeptide of HMGB1 was expressed on the surface of the vaccine vector.

In addition, methods of enhancing an immune response against influenza A and methods of reducing morbidity associated with subsequent Influenza A infection are disclosed. Briefly, the methods comprise administering to a subject a vaccine vector comprising an Influenza A epitope (an antigenic polypeptide of Influenza) capable of eliciting an immune response in an amount effective to elicit the immune response. The Influenza A epitope may be a M2e polypeptide, an HA polypeptide or a NP polypeptide or another influenza polypeptide as discussed above. The insertion of the antigenic polypeptides into the vaccine vector may be accomplished in a variety of ways known to those of skill in the art, including but not limited to the scarless site-directed mutation system described in International Patent Publication No. WO 2008/036675. The bacterium may also be engineered to express Influenza polypeptides in conjunction with polynucleotides capable of enhancing the immune response as discussed above. In particular, a polypeptide of CD154 or HMGB1 may be expressed by the vaccine vector to enhance the immune response of the subject to the influenza polypeptides. The Examples demonstrate production of a robust IgA and IgG response to vaccination in chickens. We expect that such a robust response will be protective against or at least reduce the morbidity associated with subsequent infection or challenge with the source of the antigenic polypeptide (Influenza virus in the Examples).

The compositions may be administered by a variety of means including, but not limited to, orally, intranasally, and mucosally. For example, the compositions or vaccine vectors may be delivered by aerosol, by spraying, by addition to food or water, by oral gavage, or via eye drops. In some embodiments, the compositions are administered by injection such as intradermally, parenterally, subcutaneously, intraperitoneally, intravenously, intracranially, or intramuscularly. For chickens or other poultry, the compositions may be administered in ovo.

Figure 8:
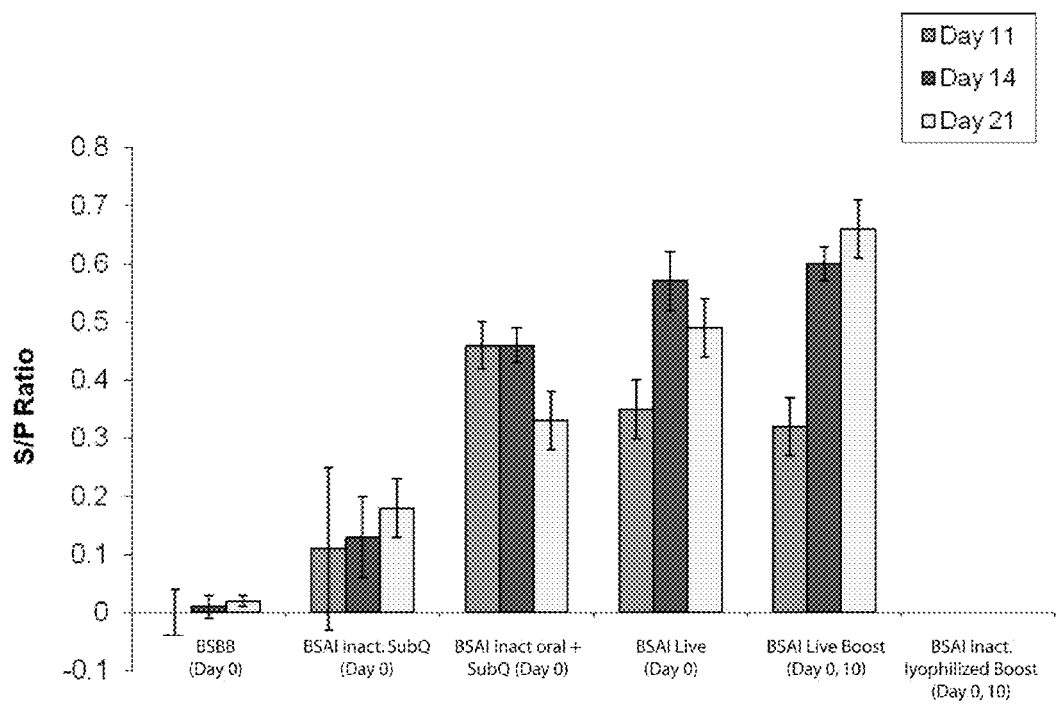
FIG. 8 is a graph showing the S/P ratios of the ELISA for M2e specific IgA antibody production by chickens vaccinated, either orally or subcutaneously, with $10^6$ live, formalin inactivated or formalin inactivated and lyophilized *Bacillus subtilis* vaccine vectors expressing the Influenza A epitopes and HMGB1 as compared to chickens vaccinated with the *Bacillus* vector alone (BSBB).

Subjects include, but are not limited to, a vertebrate, suitably a mammal, suitably a human, cows, cats, dogs, pigs, or birds, suitably poultry such as chickens. Other animal models of infection may also be used. Enhancing an immune response includes, but is not limited to, inducing a therapeutic or prophylactic effect that is mediated by the immune system of the subject. Specifically, enhancing an immune response may include enhanced production of antibodies, such as demonstrated in FIGS. 1-3, enhanced class switching of antibody heavy chains such as production of IgA as shown in FIG. 8, maturation of antigen presenting cells, stimulation of helper T cells, stimulation of cytolytic T cells or induction of T and B cell memory.

The useful dosage to be administered will vary depending on the age, weight and species of the subject, the mode and route of administration and the type of pathogen or disease against which an immune response is sought. The composition may be administered in any dose of vaccine vector sufficient to evoke an immune response. It is envisioned that doses ranging from $10^3$ to $10^{10}$ vector copies (i.e. plaque forming or colony forming units), from $10^4$ to $10^9$ vector copies, or from $10^5$ to $10^7$ vector copies are suitable.

The composition may be administered only once or may be administered two or more times to increase the immune response. For example, the composition may be administered two or more times separated by one week, two weeks, or by three weeks, one month, two months, three months, six months or more. The bacteria may be viable prior to administration, but in some embodiments the bacteria may be killed or inactivated prior to administration. In some embodiments, the bacteria may be able to replicate in the subject, while in other embodiments the bacteria may not be capable of replicating in the subject. As shown in the Examples, bacterial vaccine vectors may be inactivated prior to administration using formalin, ethanol, heat or antibiotics. One skilled in the art would appreciate other means of inactivating vaccine vectors could be used as well.

A *Bacillus* spp. vaccine vector is also provided herein. The *Bacillus* vaccine vector includes a first polynucleotide sequence encoding an antigenic polypeptide and a second polynucleotide sequence encoding an immunostimulatory polypeptide. The antigenic polypeptide and the immunostimulatory polypeptide are present on the surface of the *Bacillus* vaccine vector as described above. The antigenic polypeptide is an Influenza polypeptide as described above and the immunostimulatory polypeptide is a HMGB1 polypeptide as described above or a CD154 polypeptide.

Polynucleotides encoding immunostimulatory polypeptides that are homologous to proteins of the subject and capable of stimulating the immune system to respond to the antigenic polypeptide may also be inserted into a vaccine vector. As described in more detail in the Examples, a vaccine vector may include a CD154 polypeptide that is capable of binding CD40 in the subject and stimulating the subject to respond to the vaccine vector and its associated antigenic polypeptide, similar to HMGB1 described above. The *Bacillus* vaccine vector may include a HMGB1 polypeptide, a CD154 polypeptide or a combination thereof. As described above, polynucleotides encoding these polypeptides may be inserted into the chromosome of the vaccine vector or maintained extrachromosomally. One of skill in the art will appreciate that these polypeptides can be inserted in a variety of polypeptides of the vaccine vector and expressed in different parts of the vaccine vector or may be secreted.

The polynucleotide encoding an immunostimulatory polypeptide capable of enhancing the immune response to an antigenic polypeptide may also encode the antigenic polypeptide.

The polynucleotide encoding an immunostimulatory polypeptide may be linked to the polynucleotide encoding the antigenic polypeptide, such that in the vaccine vector the immunostimulatory polypeptide and the antigenic polypeptide are encoded by the same polynucleotide. In the Examples, a polynucleotide encoding a polypeptide of CD154, which is capable of binding to CD40, or HMGB1 also encodes an M2e epitope, an HA epitope and a NP epitope of Influenza A. See SEQ ID NOs: 19-22. In the Examples, the polynucleotide encoding the Influenza epitopes and the polynucleotide encoding the immunostimulatory polypeptide are both expressed from a plasmid for vegetative cell expression. In some embodiments, the polynucleotides are inserted in the cotB gene or another gene encoding a protein expressed on the surface of spores. Those of skill in the art will appreciate that bacterial polynucleotides encoding other transmembrane proteins may also be used.

As discussed above, a polynucleotide encoding an immunostimulatory polypeptide homologous to a protein of the subject that is capable of enhancing the immune response to the epitope may be included in the vaccine vector. In the Examples, a *Bacillus* vaccine vector including a polynucleotide encoding either a CD154 polypeptide capable of binding to CD40 or a polypeptide encoding HMGB1 were demonstrated to enhance the immune response to the M2e epitope and to two distinct HA epitopes as measured by increased antibody production in response to vaccination.

Suitably, the CD154 polypeptide is fewer than 50 amino acids long, more suitable fewer than 40, fewer than 30 or fewer than 20 amino acids in length. The polypeptide may be between 10 and 15 amino acids, between 10 and 20 amino acids or between 10 and 25 amino acids in length. The CD154 sequence and CD40 binding region are not highly conserved among the various species. The CD154 sequences of chicken and human are provided in SEQ ID NO: 11 and SEQ ID NO: 12, respectively.

The CD40 binding regions of CD154 have been determined for a number of species, including human, chicken, duck, mouse and cattle and are shown in SEQ ID NO: 13, SEQ ID NO: 14, SEQ ID NO:15, SEQ ID NO:16, SEQ ID NO:17, respectively. Although there is variability in the sequences in the CD40 binding region between species, the Examples below indicate that the human CD154 polypeptide was able to enhance the immune response in chickens. Therefore, one may practice the invention using species specific CD154 polypeptides or a heterologous CD154 polypeptide. In particular, CD154 polypeptides and functional fragments or homologs thereof include polypeptides identical to, or at least 99% identical, at least 98% identical, at least 95% identical, at least 90% identical, at least 85% identical, or at least 80% identical to the CD154 polypeptides of SEQ ID NOs: 11-17.

The *Bacillus* vaccine vector described herein may be used in the methods of enhancing an immune response and the methods of reducing Influenza morbidity in a subject as described above. The *Bacillus* vaccine vector may be used to make compositions for administration to subjects such as those described above as well.

Heterologous polynucleotides encoding antigenic polypeptides can be inserted in the bacterial genome at any non-essential site or alternatively may be carried on a plasmid using methods well known in the art. One suitable site for insertion of polynucleotides is within external portions of transmembrane proteins or coupled to sequences which target the heterologous polynucleotide for secretory pathways. Examples of a suitable transmembrane protein for insertion of polynucleotides are the cotB gene of *Bacillus* and the lamB gene of *Salmonella*.

Heterologous polynucleotides include, but are not limited to, polynucleotides encoding antigens selected from pathogenic microorganisms or viruses other than the vaccine vector. Such polynucleotides may be derived from pathogenic viruses such as influenza (e.g., M2e, hemagglutinin, or neuraminidase), herpesviruses (e.g., the genes encoding the structural proteins of herpesviruses), retroviruses (e.g., the gp160 envelope protein), adenoviruses, paramyxoviruses, coronaviruses and the like. Heterologous polynucleotides can also be obtained from pathogenic bacteria, e.g., genes encoding bacterial proteins such as toxins, and outer membrane proteins. Further, heterologous polynucleotides from parasites, such as *Eimeria* are attractive candidates for use in a vector vaccine.

Additional immunostimulatory polypeptides involved in triggering the immune system may also be included in the vaccine vectors described herein. The polynucleotides may encode immune system molecules known for their stimulatory effects, such as an interleukin, Tumor Necrosis Factor or an interferon, or another polynucleotide involved in immune-regulation.

The following examples are meant only to be illustrative and are not meant as limitations on the scope of the invention or of the appended claims.

EXAMPLES

Example 1. Construction of HA/NP/M2e/cCD154 and HA/NP/M2e/HMGB1 *Bacillus* Vectors Strains and Culture Conditions All plasmids were first maintained in TOP10 *E. coli* cells (Invitrogen, Carlsbad, Calif., USA) unless described otherwise. *Bacillus* spp. was used for introduction of mutations (*Bacillus subtilis*, Poultry Health Laboratory strain designated as NP122). Bacteria carrying plasmid pDGIEF and pHT10 were grown at 37° C.

Luria-Bertani (LB) media was used for routine growth of cells, and SOC media (Invitrogen, Carlsbad, Calif., USA) was used for phenotypic expression after electroporation. When appropriate, the following were added to the media: Isopropyl-β-D-thiogalactopyranoside (IPTG) at 1 mM, ampicillin (Amp) at 1001 µg/ml, spectinomycin (SP) at 100 µg/ml, and chloramphenicol (Cm) at 5 µg/ml.

Plasmids

Plasmids pDGIEF (*Bacillus* Genetic Stock Center, Columbus, Ohio) and pHT10 used for the present study were described previously (Zhang et al., Nuc. Acids Research 2006, 34 (9): 1-8 and Nguyen et al., Curr. Micro. 2007, 55:89-93). Plasmid pDGIEF served as a template for amplification of the mazF gene which was used as the counter-selectable marker during *Bacillus* chromosomal manipulation. Plasmid pHT10 was used to code for and produce the heterologous epitope sequences for Avian Influenza within *Bacillus* spp. This plasmid contains a CM resistance gene, is induced by the addition of 1 mM IPTG, and is maintained within *Bacillus* at 37° C.

Production of Heterologous Proteins for Vegetative Cell Expression:

Plasmid pHT10 purchased from MoBioTec/Boca Scientific, Boca Raton, Fla. (Nguyen et al., 2007) was transformed at the multiple cloning site by addition of a *Bacillus subtilis* codon optimized insertion sequence. DNA sequencing was done to confirm correct sequence insertion. The newly modified plasmid was then transformed into *Bacillus*. Briefly, *Bacillus* cultures were grown overnight at 37° C. in HS media (Spizizen's medium supplemented with 0.5% glucose, 50 µg/ml DL-tryptophan, 50 µg/ml uracil, 0.02% casein hydrolysate, 0.1% yeast extract, 8µg/ml arginine, 0.4 µg/ml histidine, 1 mM MgSO$_4$). The overnight culture (1 ml) was used to inoculate 20 ml LS medium (Spizizen's medium supplemented with 0.5% glucose, 5 µg/ml DL-tryptophane, 5 µg/ml uracil, 0.01% casein hydrolysate, 0.1% yeast extract, 1 mM MgSO$_4$, 2.5 mM MgCl$_2$, 0.5 mM CaCl$_2$) and incubated with shaking for 3-4 hours at 30° C. To 1 ml of the resulting LS culture 10 µl of 0.1M EGTA was added and incubated at room temperature for 5 minutes. Then 1-2 µg plasmid DNA was added, shaken for 2 hours at 37° C., and plated on LB plates with selective antibiotics. These transformed *Bacillus* spp. now produce heterologous epitope sequences from AI when induced with 1 mM IPTG.

PCR

All primers used for PCR are listed in Table 1. Typical PCR conditions consisted of approximately 0.1 µg of purified genomic, plasmid or PCR-generated DNA (Qiagen, Valencia, Calif., USA), 1× Pfu polymerase buffer, 5 U Pfu polymerase (Stratagene La Jolla, Calif., USA), 1 mM dNTPs (GE Healthcare Bio-Sciences Corp., Piscataway, N.J.), 1.2 µM of each primer in a total volume of 50 µL. The DNA engine thermal cycler (Bio-Rad, Hercules, Calif., USA) was used with the following amplification conditions: 94° C. for 2 minutes; 30 cycles of 94° C. sec for 30 sec, 58° C. for 60 sec, 72° C. for 90 sec per 1 kb; and 72° C. for 10 minutes for final extension. Each PCR product was gel purified (Qiagen, Valencia, Calif., USA) and either eluted in 25 µL EB buffer for preparation of templates used in overlapping extension PCR or in 50 µL EB buffer, ethanol precipitated and suspended in 5 µL of ddH$_2$O for electroporation into *Bacillus* spp.

TABLE 1

| | | Primer sequences used to generate the vaccine vector |
|---|---|---|
| Primer | Amplified Region | Primer Sequence (SEQ ID NO:) |
| mazF for | MazF gene | 5' ctaaaatcttcagatgatcaatcatcctcactgcccgctttccagtcgggaaa 3' (SEQ ID NO: 31) |
| mazF rev | MazF gene | 5' tgaacgtgacgaacgaccagatttccccctatgcaagggtttat 3' (SEQ ID NO: 32) |

TABLE 1-continued

Primer sequences used to generate the vaccine vector

| Primer | Amplified Region | Primer Sequence (SEQ ID NO:) |
|---|---|---|
| Cot B up for | Cot B up | 5' gaaatgctcgatgctgatga 3' (SEQ ID NO: 33) |
| Cot B up rev | Cot B up | 5' ggatgattgatcatctgaagattttag 3' (SEQ ID NO: 34) |
| Cot B dn for | Cot B down | 5' aaatctggtcgttcgtcacgttca 3' (SEQ ID NO: 35) |
| Cot B dn rev | Cot B down | 5' ttacgtttccagtgatagtctatcg 3' (SEQ ID NO: 36) |
| BS/AI/ HMGB1 for | BS/AI/ HMGB1 Cot B up | 5' aaccattctttcaattgtaattgaattttgaatcagtctgcctgatgatgacagttcttcataatcattaaaatc gcccggatagcacagatcatttgccggatttgctgatgatgaatccatgcctgttctaaccagtgctcttgttc tttgatatgt *ggatgattgatcatctgaagattttag* 3' (SEQ ID NO: 37) |
| BS/AI/ HMGB1 rev | BS/AI/ HMGB1 Cot B down | 5' ttacaattgaaagaatggttctgtcatcatcatcactgctgtcaagaattaatcattttgaaaaaattcaatcat catcagaagttgaaacaccgattagaaattcatcatcatggatgacaacatcatatgcaccgacatcatcatca tcagaagttgaaacaccgattagaaat*aaatctggtcgttcgtcacgttca* 3' (SEQ ID NO: 38) |
| BS/AI/ CD154 for | BS/AI/ CD154 Cot B up | 5' ttcaaaatgattaattcttgacagcagtgatgatgatgacagaaccattctttcaattgtaattgaattttgaat cagtctgcctgatgatgacagttcttcataatcattaaaatcgcccggatagcacagatcatttgccggatttg *cggatgattgatcatctgaagattttag* 3' (SEQ ID NO: 39) |
| BS/AI/ CD154 rev | BS/AI/ CD154 Cot B down | 5' caagaattaatcattttgaaaaaattcaatcatcatcagaagttgaaacaccgattagaaattcatcatcactgaaa gaaaatatgaaaaagatattgcagcatatagagcaaaaaggcaaagttgatgcaggcaaaaaagttgttgcaaa agcagaaaaatcaaaaaaaaaaat*ctggtcgttcgtcacgttca* 3' (SEQ ID NO: 40) |

In Table 1, italicized nucleotides are those which are complementary to eitehr side of the Cot B gene insertion site of *Bacillus subtilis*.

Electroporation

Briefly, cells were inoculated into 10 mL of LB broth and grown at 37° C. overnight. Then 100 µL of overnight culture was re-inoculated into 10 mL fresh LB broth at 37° C. for 3-4 hours. Cells were washed five times in ddH$_2$O water and resuspended in 60 µL of 10% glycerol. Cells were then pulsed at 2.4-2.45 kV for 1-6 ms, incubated in 0.5 ml SOC for 2-3 hours at 37° C. and plated on LB media with appropriate antibiotics.

Chromosomal Integration of Heterologous DNA for Spore Coat Expression:

Recombinant *Bacillus* strains containing stable integrated copies of selected M2e, HA and NP epitopes were constructed using recently published methods with modification. Briefly, *Bacillus* strains were transformed with the MazF cassette (Zhang et al., 2006) which generated a strain which was IPTG sensitive and spectomycin resistant. The MazF cassette flanked by approximately 300 bp of homologous DNA on each side was introduced into the CotB gene (Isticato et al., 2001) of the *Bacillus* vector by electroporation followed by growth on media containing spectomycin for positive clones which now contain the MazF cassette which is spectomycin resistant.

After the MazF mutation was confirmed in CotB, this region was replaced by a codon-optimized DNA sequence coding for the antigenic epitopes of AI again flanked by 300 bp of homologous DNA. This was done by creating a PCR product using overlapping and extension PCR to produce the antigenic sequences flanked by approximately 300 bp on each side homologous to the *Bacillus* chromosome (Cox et al., 2007). The PCR product was introduced into the *Bacillus* again by electroporation and replacement of the MazF cassette. Transformants were selected on plates containing IPTG, positive clones should now be unresponsive to IPTG and sensitive to spectomycin. Correct chromosomal sequence insertion was confirmed by DNA sequencing.

Example 2. Vaccination Study 1 and 2

Day-of-hatch (day 0) chicks were obtained from a local commercial hatchery and randomly distributed into treatment groups (n=15/treatment group, Exp 1 and n=20/treatment group, Exp 2). All chicks in each treatment group were tagged and numbered. The chicks were orally infected by gavage with 0.25 ml of saline or $10^6$-$10^8$ cfu/ml of the various *Bacillus* treatments as indicated in Table 2 for study 1 and in Table 3 for study 2.

TABLE 2

Challenge Dose for each treatment group in Vaccination Study 1.

| Treatment Group | Challenge Dose |
|---|---|
| Saline only | |
| BS/AI/HMGB1 | $10^6$ cfu/ml |
| BS/AI/HMGB1 | $10^8$ cfu/ml |
| BS/AI/CD154 | $10^6$ cfu/ml |
| BS/AI/CD154 | $10^8$ cfu/ml |

TABLE 3

Challenge Dose for each treatment group in Vaccination Study 2.

| Treatment Group | Challenge Dose |
|---|---|
| BSBB (*Bacillus*) | $10^6$ cfu/ml |
| BS/AI/HMGB1 | $10^6$ cfu/ml |
| BS/AI/CD154 | $10^6$ cfu/ml |
| BS/AI/HMGB1 Heat Inactivated | $10^6$ cfu/ml |
| BS/AI/HMGB1 Formalin Inactivated | $10^6$ cfu/ml |
| BS/AI/HMGB1 Antibiotic Inactivated | $10^6$ cfu/ml |
| BS/AI/HMGB1 Ethanol Inactivated | $10^6$ cfu/ml |

In study 2, the bacteria were inactivated in several different ways to assess whether replication was necessary for production of an antibody response directed to the antigenic influenza peptides. Several means of inactivation were used because the means of inactivation could result in destruction of the epitope and result in misinterpretation of the data and supporting a need for replication or viability of the *Bacillus* vector. The bacteria were inactivated by incubation for 10 minutes in 0.022% formalin (formalin inactivated); incubation for 10 minutes at 70° C. (heat inactivated); incubation in 5 µg/ml gentamycin (antibiotic inactivated); or incubation for 10 minutes in 70% ethanol (ethanol inactivated).

Each treatment group was housed in an individual floor pen on fresh pine litter and provided water and feed ad libitum. On days 11 and 21 post-hatch, the birds were given a booster vaccine of the same treatment they received on Day 0. Also on days 21 and 31/32, blood was collected from each of the tagged birds and the serum was removed.

The serum collected from the tagged birds in each treatment group was then used in an antibody capture ELISA to determine specific M2e, HAUA and HALB antibody response. In brief, individual wells of a 96-well plate were coated with 10 µg/ml of the M2e epitope, HAUA epitope or HALB epitope conjugated to BSA. Antigen adhesion was allowed to proceed overnight at 4° C. Plates were rinsed with PBS+0.05% Tween 20, blocked with PBS Superblock (Pierce Chemical Co.) for a minimum of 2 hours and incubated for 2 hours with the serum previously collected from the birds in each of the treatment groups described above. The plates were rinsed with PBS+0.05% Tween 20 followed by incubation with peroxidase conjugated Goat-anti-Chicken IgY secondary antibody (1:7,500 dilution) obtained from Jackson ImmunoResearch Laboratories (West Grove, Pa.) for an additional hour. After subsequent rinsing, the plates were developed using a peroxidase substrate kit obtained from Fisher Scientific and absorbances read on a spectrophotometer at 450 nm and 405 nm.

Pooled serum samples from the groups receiving the vectored vaccine were used as positive controls and pooled serum samples from the unvaccinated groups were used as negative controls on each plate to replace the serum from the treatment groups. The absorbances obtained for the positive control, negative control and experimental samples were used to calculate Sample to Positive control ratios (S/P ratios) using the following calculation:

$$S/P \text{ ratio calculation: } \frac{\text{sample mean} - \text{negative control mean}}{\text{positive control mean} - \text{negative control mean}}$$

Figure 2:
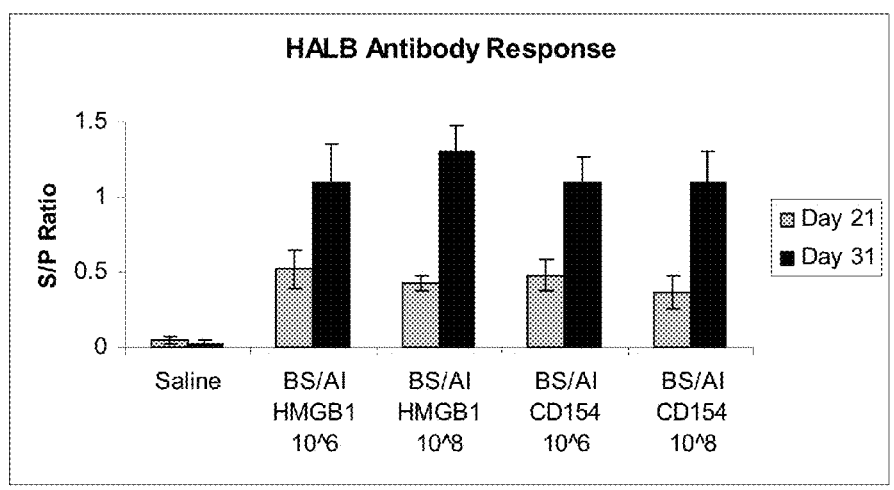
FIG. 2 is a graph showing the S/P ratios of the ELISA for HA LB specific antibody production by chickens after oral gavage of the indicated dosage of *Bacillus subtilis* vaccine vector expressing the Influenza A epitopes and either HMGB1 or CD154 as compared to chickens vaccinated with saline.
Figure 3:
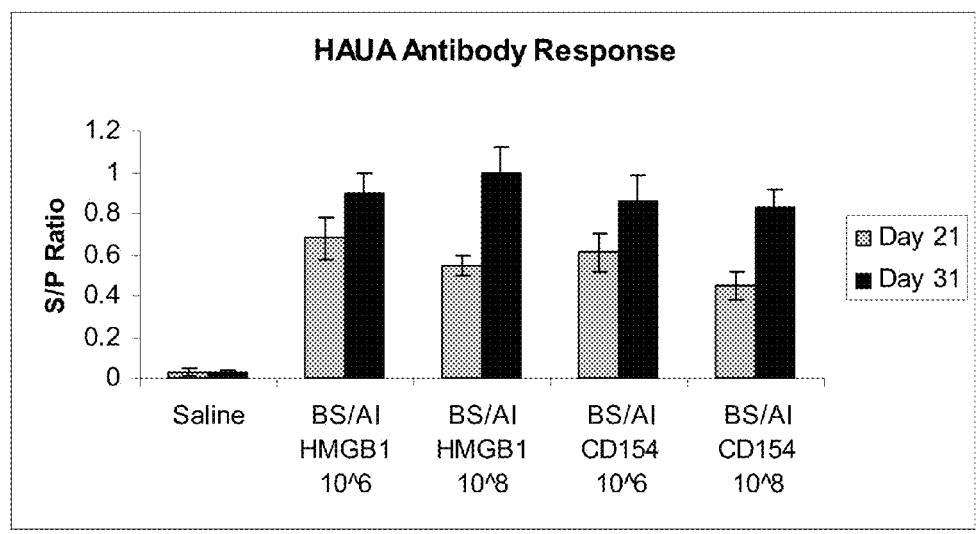
FIG. 3 is a graph showing the S/P ratios of the ELISA for HA UA specific antibody production by chickens after oral gavage of the indicated dosage of *Bacillus subtilis* vaccine vector expressing the Influenza A epitopes and either HMGB1 or CD154 as compared to chickens vaccinated with saline.
Figure 4:
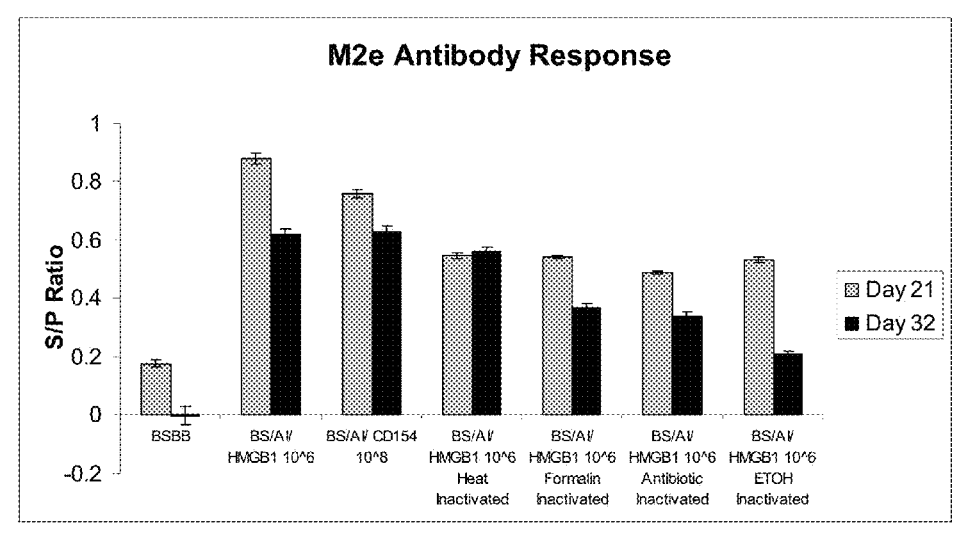
Figure 5:
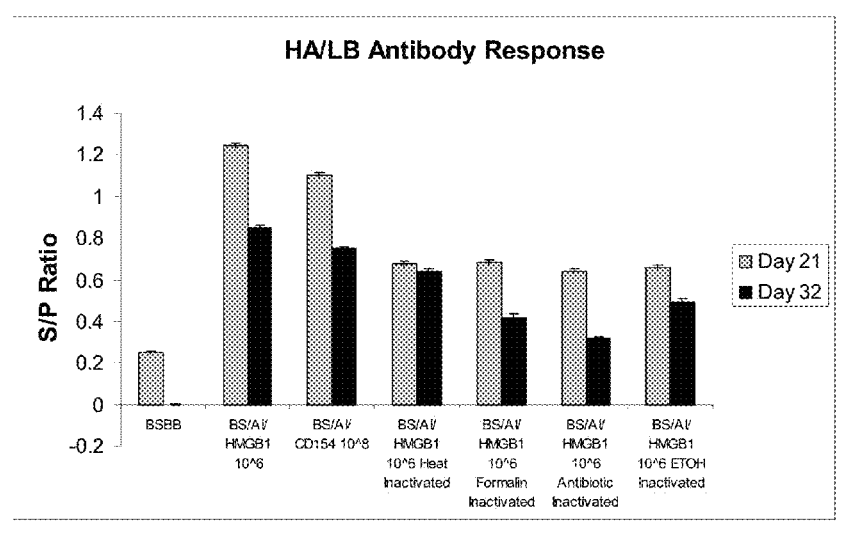
Figure 6:
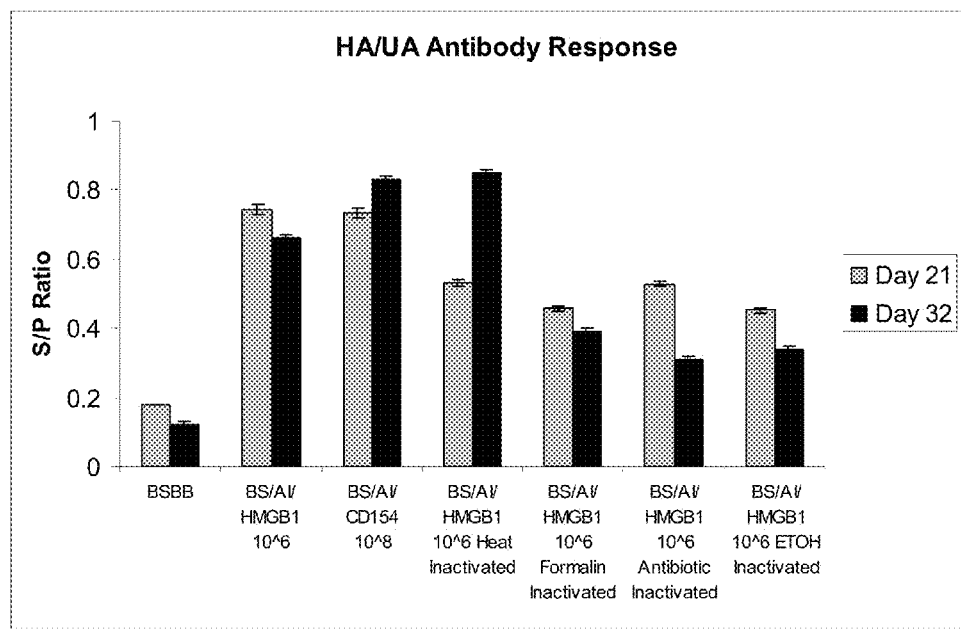
FIG. 6 is a graph showing the S/P ratios of the ELISA for HA UA specific antibody production by chickens after oral gavage of the indicated dosage of live or variously inactivated *Bacillus subtilis* vaccine vectors expressing the Influenza A epitopes and either HMGB1 or CD154 as compared to chickens vaccinated with the *Bacillus* vector alone (BSBB).

The calculated S/P ratios for each study are shown in FIGS. 1-6. FIGS. 1-3 show the total antibody titers for M2e, HALB and HAUA for study 1, respectively, at days 21 and 31 post-hatch. The results demonstrate that robust immune responses to each of these antigens were generated after oral administration with a *Bacillus* expressing each of the epitopes with either CD154 of HMGB1 as the immunostimulatory peptide. FIGS. 4-6 show the total antibody titers for M2e, HALB and HAUA for study 2, respectively, at days 21 and 32 post-hatch. The results demonstrate that robust immune responses to each of the epitopes were generated after oral administration of a live *Bacillus* expressing the epitope and an immunostimulatory peptide. FIGS. 4-6 also demonstrate that similar levels of specific antibodies were generated when the vector (the *Bacillus*) was inactivated prior to administration.

Example 3. Vaccination Study 3

Figure 7:
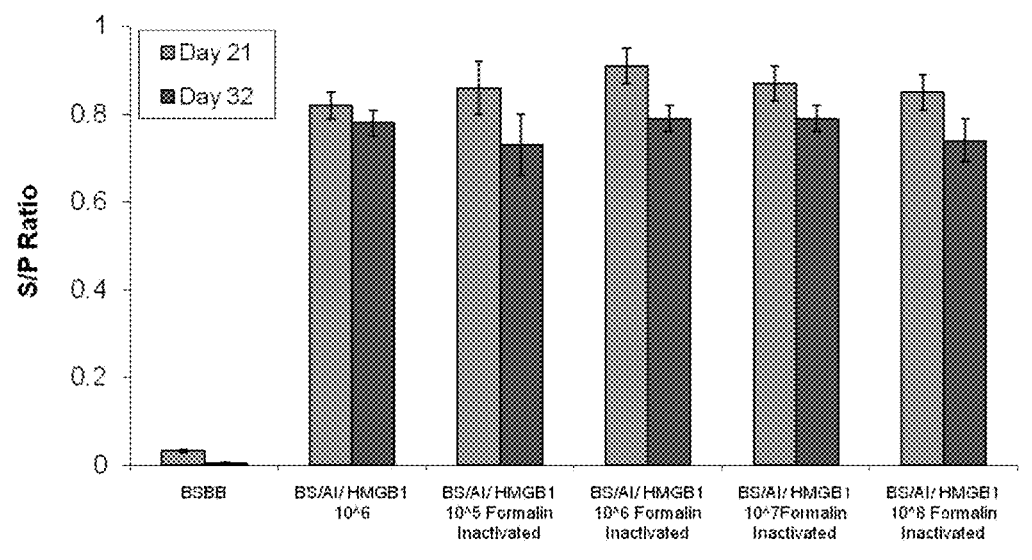

Day-of-hatch (day 0) chicks were obtained from a local commercial hatchery and randomly distributed into treatment groups (n=20/treatment group). All chicks in each treatment group were tagged and numbered. The chicks were orally infected by gavage with 0.25 ml of saline or $10^5$-$10^8$ cfu/ml of the *Bacillus* vector (BSBB), the *Bacillus* vector expressing the avian influenza epitopes and HMGB1 (BS/AI/HMGB1), or various amounts of the BS/AI/HMGB1 vector after formalin inactivation (as described above). On day 10 post-hatch, the birds were given a booster vaccine of the same treatment they received on Day 0. Also on days 21 and 32, blood was collected from each of the tagged birds and the serum was removed. The serum IgG M2e specific antibody levels were determined using the method described above with a peroxidase labeled anti-chicken IgG specific secondary antibody (Jackson ImmunoResearch Laboratories, West Grove, Pa.). The results in FIG. 7 show that the formalin inactivated bacteria were able to stimulate production of M2e specific IgG antibodies as well as live bacteria. This result was surprising because it was generally believed that only live bacteria could stimulate a robust immune response after oral administration.

Example 4. Vaccination Study 4

Figure 9:
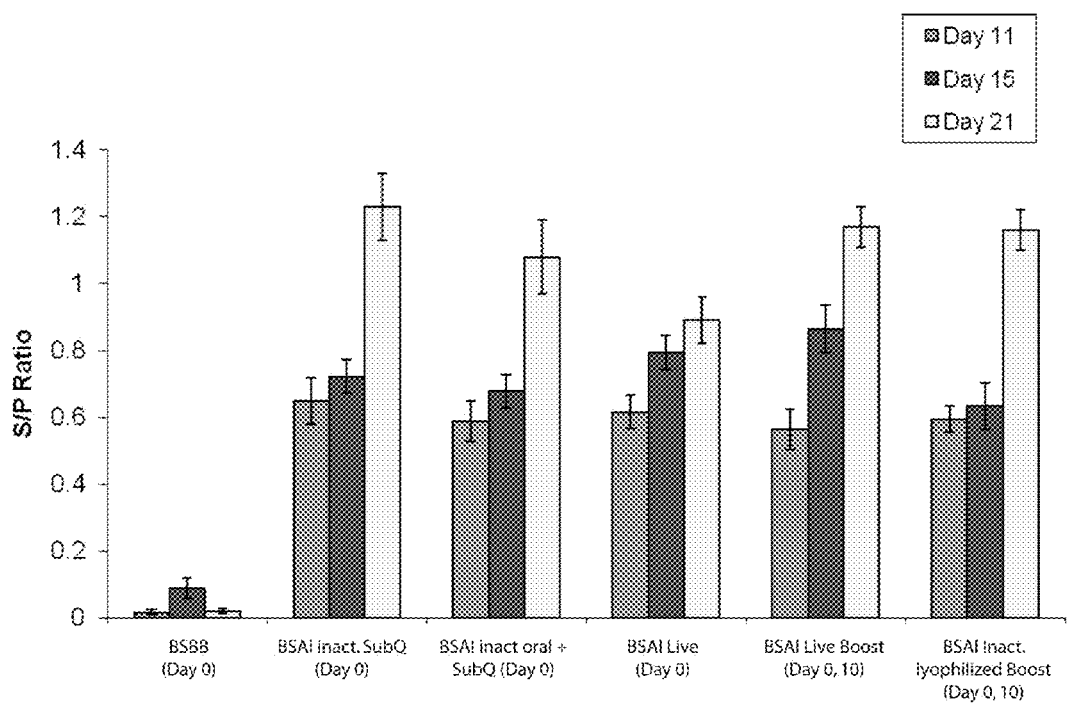

Day-of-hatch (day 0) chicks were obtained from a local commercial hatchery and randomly distributed into treatment groups (n=20-35/treatment group). All chicks in each treatment group were tagged and numbered. The chicks were orally infected by gavage or injected sub-cutaneously with 0.25 ml of $10^6$ cfu/ml of the *Bacillus* vector (BSBB), the *Bacillus* vector expressing the avian influenza epitopes and HMGB1 (BSAI), or the BSAI vector after formalin inactivation (as described above) or after formalin inactivation followed by lyophilization (reconstituted with saline immediately prior to administration). On day 10 post-hatch, some of the birds were given a booster vaccine of the same treatment they received on Day 0. On days 11, 14 and 21, blood was collected from each of the tagged birds and the serum was removed. The serum IgA and IgG M2e specific antibody levels were determined using the method described above with a peroxidase labeled anti-chicken IgA (GenTex) or a peroxidase labeled anti-chicken IgG specific secondary antibody (Jackson ImmunoResearch Laboratories, West Grove, Pa.). The results in FIG. 8 show that the formalin inactivated bacteria were able to stimulate production of M2e specific IgA antibodies about as well as live bacteria when given orally. In contrast when given sub-cutaneously the inactivated BSAI vector was not as efficient at stimulating an IgA antibody response and the lyophilized bacteria did not stimulate an IgA response. The results in FIG. 9 show that each of the BSAI administration protocols supported robust IgG formation.

We claim:

1. A vaccine vector comprising a surface, a first polynucleotide encoding an antigenic polypeptide, and a second polynucleotide encoding an HMGB1 polypeptide comprising an amino acid sequence having at least 90% identity to any one of SEQ ID NOs: 18, 23-30, wherein the antigenic polypeptide and the HMGB1 polypeptide are present on the surface of the vaccine vector.

2. The vaccine vector of claim 1, wherein the antigenic polypeptide is an Influenza specific polypeptide.

3. The vaccine vector of claim 2, wherein the antigenic polypeptide is an M2e, HA or NP Influenza polypeptide.

4. The vaccine vector of claim 3, wherein the Influenza M2e polypeptide is selected from the group consisting of SEQ ID NO:1, SEQ ID NO:2, SEQ ID NO:3, SEQ ID NO:4, SEQ ID NO:5, SEQ ID NO:6, an immunogenic fragment of SEQ ID NO:1, an immunogenic fragment of SEQ ID NO:2, an immunogenic fragment of SEQ ID NO:3 and an immunogenic fragment of SEQ ID NO:4.

5. The vaccine vector of claim 3, wherein the antigenic polypeptide is selected from the group consisting of SEQ ID NO: 7, SEQ ID NO: 8, SEQ ID NO: 9, SEQ ID NO: 10 and an immunogenic fragment of SEQ ID NO: 7, SEQ ID NO: 8, SEQ ID NO: 9, or SEQ ID NO: 10.

6. The vaccine vector of claim 1, wherein the vaccine vector is a bacterium.

7. The vaccine vector of claim 6, wherein the bacterium is *Bacillus* spp.

8. The vaccine vector of claim 1, wherein the antigenic polypeptide and the HMGB1 polypeptide are comprised within a transmembrane protein on the surface of the vaccine vector.

9. The vaccine vector of claim 8, wherein the antigenic polypeptide and the HMGB1 polypeptide are comprised within an external loop of the transmembrane protein.

10. The vaccine vector of claim 8, wherein the transmembrane protein is cotB.

11. The vaccine vector of claim 1, wherein the antigenic polypeptide and the HMGB1 polypeptide are part of a fusion protein.

12. A method of inducing an immune response in a subject comprising administering to the subject the vaccine vector of claim 1 in an amount effective to enhance the immune response of the subject to the antigenic polypeptide.

13. The method of claim 12, wherein the vaccine vector is administered orally or intranasally.

14. The method of claim 13, wherein the immune response is an IgA antibody response to the antigenic polypeptide.

15. The method of claim 14, wherein the vaccine vector is not capable of replication in the subject.

16. The method of claim 12, wherein the subject is a poultry or a mammal.

17. The method of claim 16, wherein the subject is a chicken.

* * * * *